(12) United States Patent
Imada et al.

(10) Patent No.: US 10,577,449 B2
(45) Date of Patent: Mar. 3, 2020

(54) PHENOLIC-HYDROXYL-GROUP-CONTAINING NOVOLAC RESIN AND RESIST FILM

(71) Applicant: DIC Corporation, Tokyo (JP)

(72) Inventors: Tomoyuki Imada, Ichihara (JP); Yusuke Sato, Ichihara (JP)

(73) Assignee: DIC Corporation, Tokyo (JP)

( * ) Notice: Subject to any disclaimer, the term of this patent is extended or adjusted under 35 U.S.C. 154(b) by 105 days.

(21) Appl. No.: 15/568,171

(22) PCT Filed: Apr. 21, 2016

(86) PCT No.: PCT/JP2016/062614
§ 371 (c)(1),
(2) Date: Oct. 20, 2017

(87) PCT Pub. No.: WO2016/185865
PCT Pub. Date: Nov. 24, 2016

(65) Prior Publication Data
US 2018/0134834 A1    May 17, 2018

(30) Foreign Application Priority Data
May 20, 2015 (JP) .................................. 2015-102808

(51) Int. Cl.
| | |
|---|---|
| *C08G 8/20* | (2006.01) |
| *C08G 8/04* | (2006.01) |
| *C08G 8/24* | (2006.01) |
| *G03F 7/023* | (2006.01) |
| *C07C 39/16* | (2006.01) |
| *G03F 7/039* | (2006.01) |
| *G03F 7/038* | (2006.01) |

(52) U.S. Cl.
CPC ................ *C08G 8/20* (2013.01); *C07C 39/16* (2013.01); *C08G 8/04* (2013.01); *C08G 8/24* (2013.01); *G03F 7/0236* (2013.01); *G03F 7/039* (2013.01); *G03F 7/038* (2013.01)

(58) Field of Classification Search
CPC .... C08G 8/20; C08G 8/24; C08G 8/04; G03F 7/0236; G03F 7/039; C07C 39/16
See application file for complete search history.

(56) References Cited

U.S. PATENT DOCUMENTS

| | | | | |
|---|---|---|---|---|
| 5,468,590 | A | * 11/1995 | Hashimoto et al. | ..... C08G 8/24 430/165 |
| 8,846,297 | B2 | * 9/2014 | Imada et al. | ............ C08G 8/08 430/270.1 |
| 2017/0121444 | A1 | * 5/2017 | Imada et al. | ............ C08G 8/08 |

FOREIGN PATENT DOCUMENTS

| | | |
|---|---|---|
| JP | 02-055359 A | 2/1990 |
| JP | 09-194413 A | 7/1997 |
| WO | WO-2015141427 A1 * 9/2015 | ............... C08G 8/08 |

OTHER PUBLICATIONS

International Search Report dated Jul. 5, 2016, issued for PCT/JP2016/062614.

* cited by examiner

*Primary Examiner* — Cynthia Hamilton
(74) *Attorney, Agent, or Firm* — Locke Lord LLP; James E. Armstrong, IV; Nicholas J. DiCeglie, jr.

(57) ABSTRACT

There are provided a phenolic-hydroxyl-group-containing novolac resin and resist film that are excellent in developability, heat resistance, and conformability to substrates. The phenolic-hydroxyl-group-containing novolac resin is a polycondensate of which the essential reactive components are a phenolic-hydroxyl-group-containing compound (A) represented by Structural Formula (1) [where Ar is a structural part represented by Structural Formula (Ar-1) or (Ar-2), a phenolic-hydroxyl-group-containing compound (B) represented by Structural Formula (2) [where $R^3$ is an aliphatic hydrocarbon group having 4 to 20 carbon atoms, and j is an integer from 1 to 3], and an aldehyde compound (C).

14 Claims, 4 Drawing Sheets minute minute minute minute

PHENOLIC-HYDROXYL-GROUP-CONTAINING NOVOLAC RESIN AND RESIST FILM

TECHNICAL FIELD

The present invention relates to a phenolic-hydroxyl-group-containing novolac resin that is excellent in developability, heat resistance, and conformability to substrates and to a resist film formed of such a resin.

BACKGROUND ART

Phenolic-hydroxyl-group-containing resins are used in adhesives, shaping materials, coating materials, photoresist materials, materials for producing epoxy resins, and curing agents for epoxy resins. Furthermore, such resins enable production of curing products having an excellent heat resistance and moisture resistance and are therefore widely used as curable compositions of which the main agents are phenolic-hydroxyl-group-containing resins themselves or as curing agents for epoxy or another resin in the electric and electronic fields, such as in sealing material of semiconductor devices and insulating materials of printed circuit boards.

In the field of photoresists, a variety of techniques for forming a resist pattern, which are used in different target areas on the basis of applications and functions, have been increasingly developed these days, which enhances and diversifies the demand performance of resin materials for the resist. The resin materials, for example, need to have a high developability that enables fine patterns to be accurately formed on highly integrated semiconductor devices at high efficiency. In addition, the resin materials need to impart properties, such as flexibility and durability, to cured products in the case of forming thick films; need to have resistance to dry etching and heat resistance in the case where they are used in resist underlayer films; and need to have toughness, such as conformability to substrates, as well as heat resistance in the case where they are used in permanent resist films.

Among phenolic-hydroxyl-group-containing resins, the resins most widely used in photoresists are cresol novolac resins; however, such resins do not satisfy the market demands for performance that has been enhanced and diversified as described above and do not have a sufficient heat resistance and developability (see Patent Literature 1).

CITATION LIST

Patent Literature

PTL 1: Japanese Unexamined Patent Application Publication No. 2-55359

SUMMARY OF INVENTION

Technical Problem

It is an object of the present invention to provide a phenolic-hydroxyl-group-containing novolac resin that is excellent in developability, heat resistance, and conformability to substrates. It is another object of the present invention to provide a photosensitive composition, curable composition, and resist film containing such a resin.

Solution to Problem

The inventors have intensively studied to achieve the above-mentioned objects and found that a phenolic-hydroxyl-group-containing triarylmethane compound and a phenolic-hydroxyl-group-containing compound having an aliphatic hydrocarbon group with 4 to 20 carbon atoms are turned into novolac to produce a phenolic-hydroxyl-group-containing novolac resin and that such a resin is excellent in developability, heat resistance, and conformability to substrates, thereby accomplishing the present invention.

In particular, the present invention relates to a phenolic-hydroxyl-group-containing novolac resin that is a polycondensate of which the essential reactive components are a phenolic-hydroxyl-group-containing compound (A) represented by Structural Formula (1)

[Chem. 1]

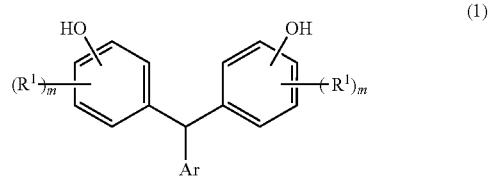

[where Ar is a structural part represented by Structural Formula (Ar-1) or (Ar-2)

[Chem. 2]

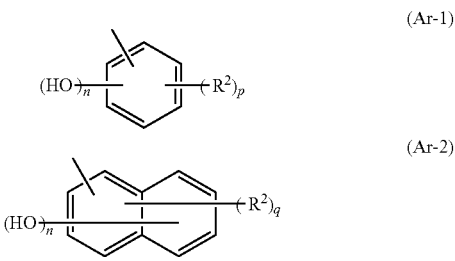

(where n in each formula is independently an integer from 0 to 2; p is an integer from 0 to 5; q is an integer from 0 to 7; and $R^2$ in each formula is independently a hydrogen atom, an alkyl group, an alkoxy group, an aryl group, an aralkyl group, or a halogen atom);

R's are each independently a hydrogen atom, an alkyl group, an alkoxy group, an aryl group, an aralkyl group, or a halogen atom; and m's are each independently an integer from 0 to 4], a phenolic-hydroxyl-group-containing compound (B) represented by Structural Formula (2)

[Chem. 3]

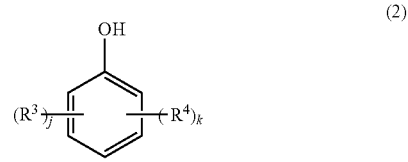

[where $R^3$ is an aliphatic hydrocarbon group having 4 to 20 carbon atoms; j is an integer from 1 to 3; $R^4$ is each independently a hydrogen atom, an alkyl group having 1 to 3 carbon atoms, an alkoxy group, an aryl group, an aralkyl group, or a halogen atom; k is an integer from 0 to (5-j)], and an aldehyde compound (C).

The present invention also relates to a phenolic-hydroxyl-group-containing novolac resin having repeating units that are a structural part (a) represented by Structural Formula (3)

[Chem. 4]

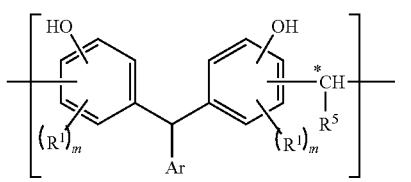

(3)

[where Ar is a structural part represented by Structural Formula (Ar-3) or (Ar-4)

[Chem. 5]

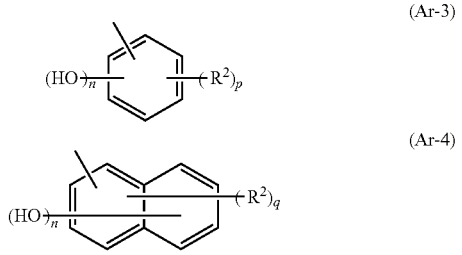

(Ar-3)

(Ar-4)

(where n in each formula is independently an integer from 0 to 2; p is an integer from 0 to 5; q is an integer from 0 to 7; and R² in each formula is independently a hydrogen atom, an alkyl group, an alkoxy group, an aryl group, an aralkyl group, a halogen atom, or a linking point that connects with the structural part represented by Structural Formula (3) or (4) via the carbon atom denoted by the symbol *);
R¹'s are each independently a hydrogen atom, an alkyl group, an alkoxy group, an aryl group, an aralkyl group, or a halogen atom; m's are each independently an integer from 0 to 4; and R⁵ is a hydrogen atom, an alkyl group, or an aryl group] and
a structural part (b) represented by Structural Formula (4)

[Chem. 6]

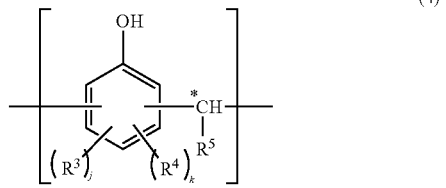

(4)

[where R³ is an aliphatic hydrocarbon group having 4 to 20 carbon atoms; j is an integer from 1 to 3; R⁴ is each independently a hydrogen atom, an alkyl group having 1 to 3 carbon atoms, an alkoxy group, an aryl group, an aralkyl group, a halogen atom, or a linking point that connects with the structural part represented by Structural Formula (3) or (4) via the carbon atom denoted by the symbol *; k is an integer from 0 to (5-j); and R⁵ is a hydrogen atom, an alkyl group, or an aryl group].

The present invention also relates to a photosensitive composition containing the above-mentioned phenolic-hydroxyl-group-containing novolac resin and a photosensitizer.

The present invention also relates to a resist film containing the above-mentioned photosensitive composition.

The present invention also relates to a curable composition containing the above-mentioned phenolic-hydroxyl-group-containing novolac resin and a curing agent.

The present invention also relates to a resist underlayer film containing the above-mentioned curable composition.

The present invention also relates to a permanent resist film containing the above-mentioned curable composition.

Advantageous Effects of Invention

The present invention can provide a phenolic-hydroxyl-group-containing novolac resin that is excellent in developability, heat resistance, and conformability to substrates. The present invention can also provide a photosensitive composition, curable composition, and resist film each containing such a resin.

DESCRIPTION OF EMBODIMENTS

Figure 1:
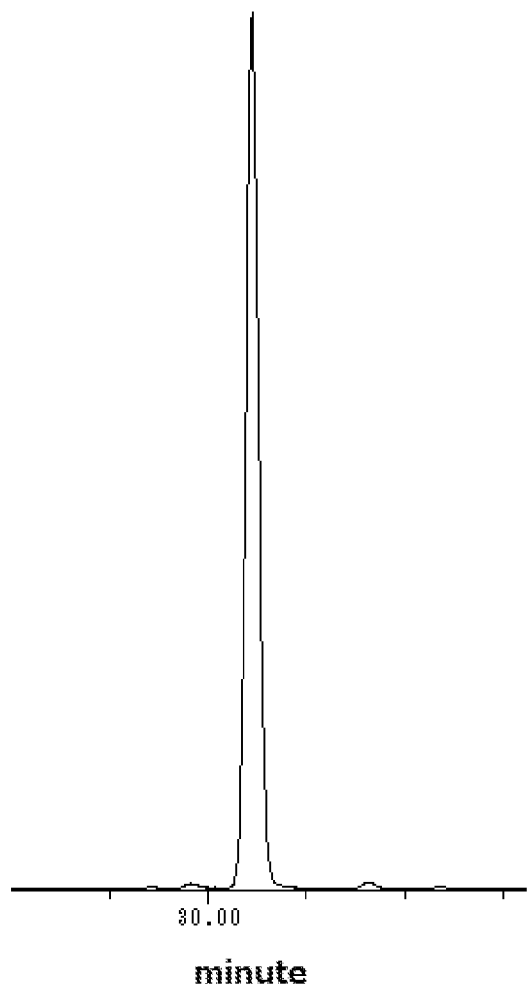
FIG. 1 is a GPC chart of a phenolic-hydroxyl-group-containing compound (A-1) produced in Production Example 1.

The present invention will now be described in detail.

The phenolic-hydroxyl-group-containing novolac resin of the present invention is a polycondensate of which the essential reactive components are a phenolic-hydroxyl-group-containing compound (A) represented by Structural Formula (1)

[Chem. 7]

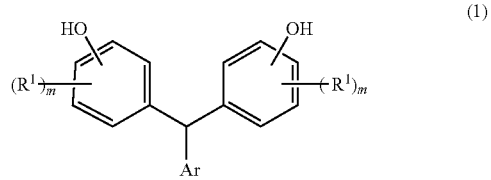

(1)

[where Ar is a structural part represented by Structural Formula (Ar-1) or (Ar-2)

[Chem. 8]

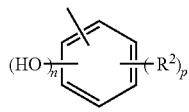
(Ar-1)

[Chem. 10]

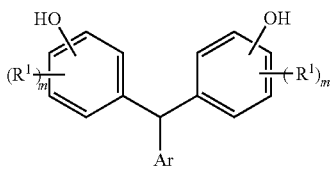
(1)

[where Ar is a structural part represented by Structural Formula (Ar-1) or (Ar-2)

[Chem. 11]

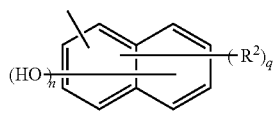
(Ar-2)

(where n in each formula is independently an integer from 0 to 2; p is an integer from 0 to 5; q is an integer from 0 to 7; and $R^2$ in each formula is independently a hydrogen atom, an alkyl group, an alkoxy group, an aryl group, an aralkyl group, or a halogen atom);
$R^1$'s are each independently a hydrogen atom, an alkyl group, an alkoxy group, an aryl group, an aralkyl group, or a halogen atom; and m's are each independently an integer from 0 to 4],
a phenolic-hydroxyl-group-containing compound (B) represented by Structural Formula (2)

[Chem. 9]

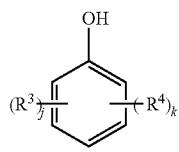
(2)

[where $R^3$ is an aliphatic hydrocarbon group having 4 to 20 carbon atoms; j is an integer from 1 to 3; $R^4$ is each independently a hydrogen atom, an alkyl group having 1 to 3 carbon atoms, an alkoxy group, an aryl group, an aralkyl group, or a halogen atom; k is an integer from 0 to (5-j)], and an aldehyde compound (C).

The phenolic-hydroxyl-group-containing compound (A) has a highly symmetric and rigid triarylmethane structure and contains phenolic hydroxyl groups at high density; hence, the phenolic-hydroxyl-group-containing novolac resin produced by using such a compound has a high heat resistance and excellent developability. This compound and the phenolic-hydroxyl-group-containing compound (B) are turned into novolac in the present invention to produce a phenolic-hydroxyl-group-containing novolac resin that has properties inherent in the phenolic-hydroxyl-group-containing compound (A) and that is excellent in stiffness and flexibility.

The phenolic-hydroxyl-group-containing compound (A) is represented by Structural Formula (1)

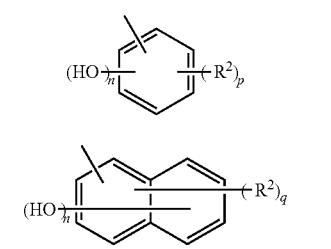
(Ar-1)

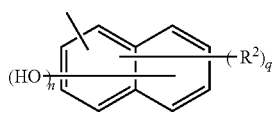
(Ar-2)

(where n in each formula is independently an integer from 0 to 2; p is an integer from 0 to 5; q is an integer from 0 to 7; and $R^2$ in each formula is independently an alkyl group, an alkoxy group, an aryl group, an aralkyl group, or a halogen atom);
$R^1$'s are each independently a hydrogen atom, an alkyl group, an alkoxy group, an aryl group, an aralkyl group, or a halogen atom; and m's are each independently an integer from 0 to 4].

In production of the phenolic-hydroxyl-group-containing novolac resin of the present invention, the phenolic-hydroxyl-group-containing compound (A) that is to be used may be one of compounds represented by Structural Formula (1) or a combination of two or more thereof.

$R^1$'s in Structural Formula (1) each independently represent an alkyl group, an alkoxy group, an aryl group, an aralkyl group, or a halogen atom. Examples of the alkyl group include a methyl group, an ethyl group, a propyl group, a butyl group, a pentyl group, a hexyl group, and a cyclohexyl group. Examples of the alkoxy group include a methoxy group, an ethoxy group, a propyloxy group, a butoxy group, a pentyloxy group, a hexyloxy group, and a cyclohexyloxy group. Examples of the aryl group include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group. Examples of the aralkyl group include a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group. Examples of the halogen atom include a fluorine atom, a chlorine atom, and a bromine atom.

Among these, $R^1$'s are each preferably an alkyl group because it enables production of a phenolic-hydroxyl-groupcontaining novolac resin having a well-balanced heat resistance and developability, and more preferably a methyl group because it gives enhanced heat resistance owing to inhibition of molecular motions, has an excellent electrodonicity to an aromatic nuclear, and is easy to be industrially obtained.

m's in Structural Formula (1) are each independently an integer from 0 to 4; in particular, they are each preferably 1 or 2 because it enables production of a phenolic-hydroxyl-group-containing novolac resin having a well-balanced heat resistance and developability.

In Structural Formula (1), the positions of the two phenolic hydroxyl groups are preferably para-positions to a methine group that joins the three aromatic rings because it enables production of a phenolic-hydroxyl-group-containing novolac resin having an excellent heat resistance.

Ar in Structural Formula (1) is a structural part represented by Structural Formula (Ar-1) or (Ar-2). In particular, a structural part represented by Structural Formula (Ar-1) is preferred because it enables production of a phenolic-hydroxyl-group-containing novolac resin having a further enhanced developability.

$R^2$ in each of Structural Formulae (Ar-1) and (Ar-2) is independently a hydrogen atom, an alkyl group, an alkoxy group, an aryl group, an aralkyl group, or a halogen atom. Examples of the alkyl group include a methyl group, an ethyl group, a propyl group, a butyl group, a pentyl group, a hexyl group, and a cyclohexyl group. Examples of the alkoxy group include a methoxy group, an ethoxy group, a propyloxy group, a butoxy group, a pentyloxy group, a hexyloxy group, and a cyclohexyloxy group. Examples of the aryl group include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group. Examples of the aralkyl group include a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group. Examples of the halogen atom include a fluorine atom, a chlorine atom, and a bromine atom.

Among these, $R^2$ is preferably a hydrogen atom or an alkyl group because it enables production of a phenolic-hydroxyl-group-containing novolac resin having a well-balanced heat resistance and developability, and more preferably a hydrogen atom because it enables easy production of the aromatic compound (A).

Specific Examples of the phenolic-hydroxyl-group-containing compound (A) represented by Structural Formula (1) include compounds having molecular structures represented by Structural Formulae (1-1) to (1-16).

[Chem. 12]

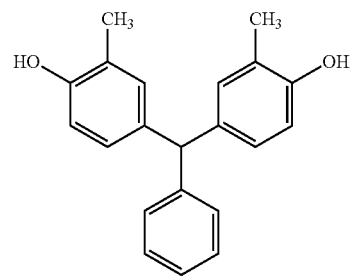

(1-1)

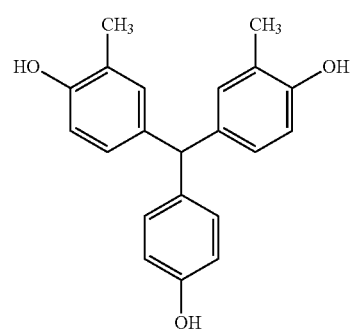

(1-2)

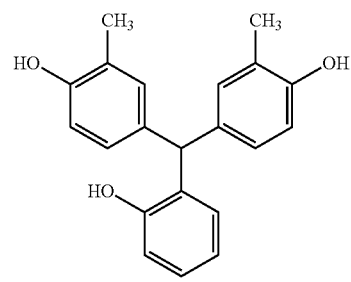

(1-3)

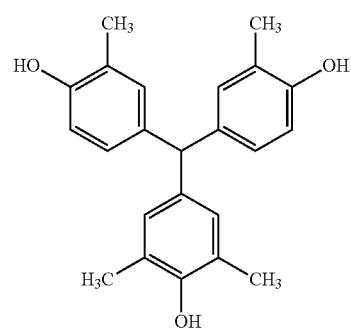

(1-4)

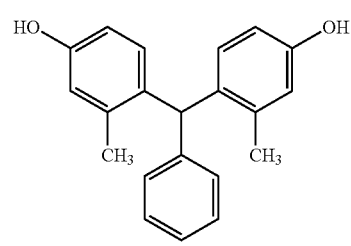

(1-5)

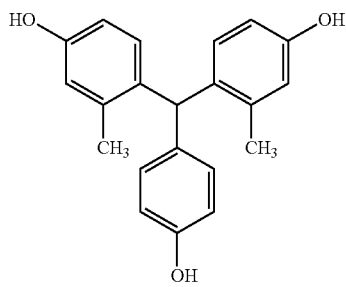 (1-6)
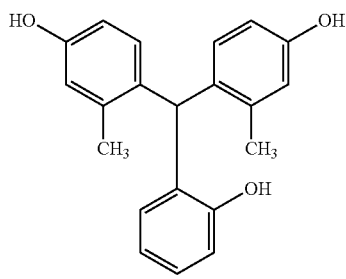 (1-7)
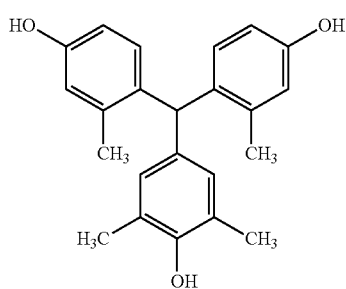 (1-8)
[Chem. 13]
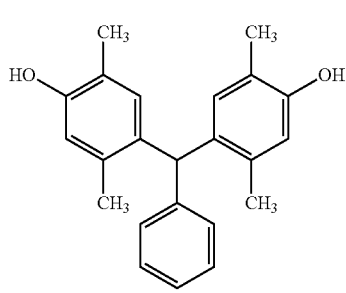 (1-9)
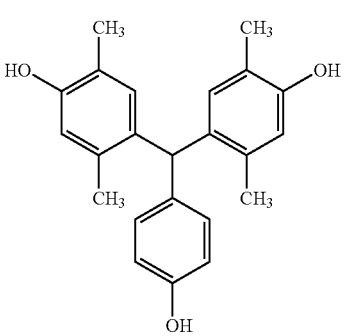 (1-10)
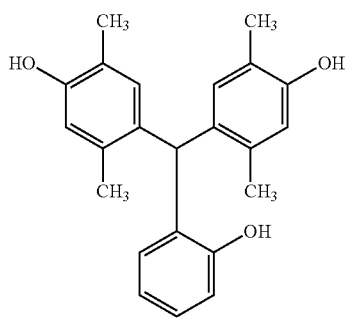 (1-11)
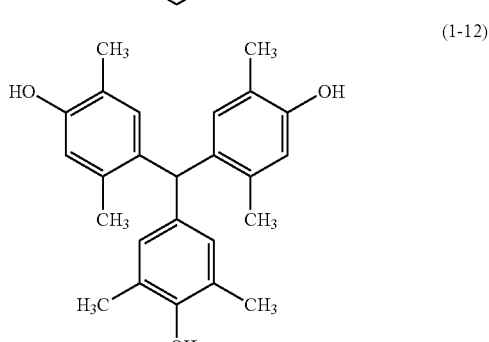 (1-12)
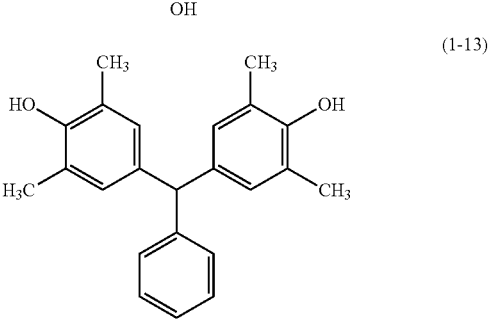 (1-13)
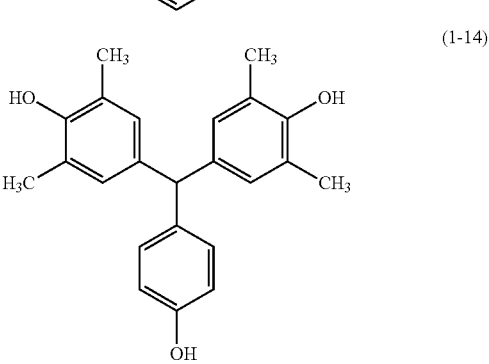 (1-14)
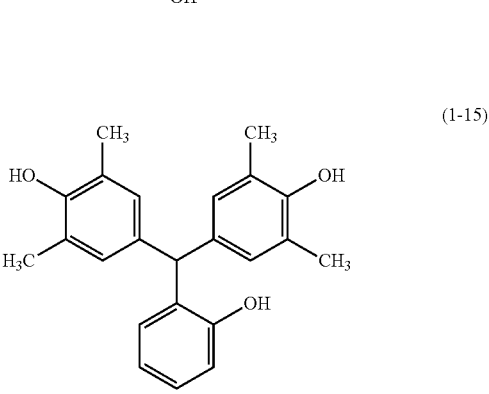 (1-15)

-continued (1-16)

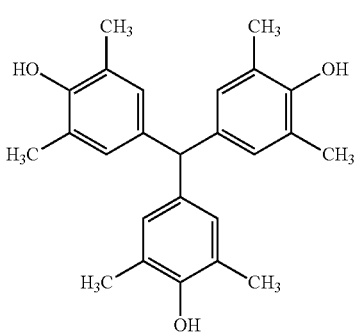

The phenolic-hydroxyl-group-containing compound (A) can be produced by, for example, the reaction of a phenolic compound (a1) with an aromatic aldehyde (a2) in the presence of an acid catalyst.

The phenolic compound (a1) is a compound of which some or all of the hydrogen atoms of the phenol or the aromatic ring of the phenol are substituted with any of an alkyl group, an alkoxy group, an aryl group, an aralkyl group, and a halogen atom. Examples of the alkyl group include a methyl group, an ethyl group, a propyl group, a butyl group, a pentyl group, a hexyl group, and a cyclohexyl group. Examples of the alkoxy group include a methoxy group, an ethoxy group, a propyloxy group, a butoxy group, a pentyloxy group, a hexyloxy group, and a cyclohexyloxy group. Examples of the aryl group include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group. Examples of the aralkyl group include a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group. Examples of the halogen atom include a fluorine atom, a chlorine atom, and a bromine atom. Such phenolic compounds (a1) may be used alone or in combination.

In particular, an alkyl-substituted phenol is preferred because it enables production of a phenolic-hydroxyl-group-containing novolac resin having well-balanced heat resistance and developability. Specific examples thereof include o-cresol, m-cresol, p-cresol, 2,5-xylenol, 3,5-xylenol, 3,4-xylenol, 2,4-xylenol, 2,6-xylenol, 2,3,5-trimethylphenol, and 2,3,6-trimethylphenol. Among these, 2,5-xylenol and 2,6-xylenol are especially preferred because they enable production of a modified novolac phenolic resin.

Examples of the aromatic aldehyde (a2) include benzaldehyde; hydroxybenzaldehyde compounds such as salicylaldehyde, m-hydroxybenzaldehyde, and p-hydroxybenzaldehyde; dihydroxybenzaldehyde such as 2,4-dihydroxybenzaldehyde and 3,4-dihydroxybenzaldehyde; vanillin compounds such as vanillin, ortho-vanillin, isovanillin, and ethyl vanillin; and hydroxynaphthaldehyde compounds such as 2-hydroxy-1-naphthaldehyde and 6-hydroxy-2-naphthaldehyde. These may be used alone or in combination.

Among these aromatic aldehydes (a2), hydroxybenzaldehyde compounds or hydroxynaphthaldehyde compounds are preferred, and p-hydroxybenzaldehyde is especially preferred because they enable production of a phenolic-hydroxyl-group-containing novolac resin having well-balanced heat resistance and developability.

The reaction molar ratio [(a1)/(a2)] of the phenolic compound (a1) to the aromatic aldehyde (a2) is preferably in the range of 1/0.2 to 1/0.5, and more preferably 1/0.25 to 1/0.45 because the intended aromatic compound (A) can be produced in high yield and high purity.

Examples of the acid catalyst used in the reaction of the phenolic compound (a1) with the aromatic aldehyde (a2) include acetic acid, oxalic acid, sulfuric acid, hydrochloric acid, phenolsulfonic acid, para-toluenesulfonic acid, zinc acetate, and manganese acetate. These acid catalysts may be used alone or in combination. Among these, sulfuric acid and para-toluenesulfonic acid are preferred because they are excellent in catalytic activity.

The reaction of the phenolic compound (a1) with the aromatic aldehyde (a2) may be optionally performed in an organic solvent. Examples of the solvent that is to be used include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxaene, 1,4-dioxane, and tetrahydrofuran; glycol esters such as ethylene glycol acetate; and ketones such as acetone, methyl ethyl ketone, and methyl isobutyl ketone. These solvents may be used alone or in the form of a mixed solvent of two or more. Among these, 2-ethoxyethanol is preferred because the aromatic compound (A) that is to be produced has an excellent solubility.

The reaction of the phenolic compound (a1) with the aromatic aldehyde (a2) is, for example, performed at a temperature ranging from 60 to 140° C. for a duration of 0.5 to 100 hours.

After the termination of the reaction, the unreacted phenolic compound (a1) and aromatic aldehyde (a2) and the acid catalyst used can be removed from the reaction product through, for example, the following process to yield the purified phenolic-hydroxyl-group-containing compound (A): the reaction product is poured into a poor solvent (S1) for the phenolic-hydroxyl-group-containing compound (A), the precipitate is separated by filtration, and then the resulting precipitate is re-dissolved in a solvent (S2) in which the phenolic-hydroxyl-group-containing compound (A) is highly soluble and which is miscible with the poor solvent (S1).

In the case where the reaction of the phenolic compound (a1) with the aromatic aldehyde (a2) is performed in an aromatic hydrocarbon solvent such as toluene or xylene, the reaction product is heated to 80° C. or more to dissolve the phenolic-hydroxyl-group-containing compound (A) in the aromatic hydrocarbon solvent, and the resulting product is cooled in this state, thereby being able to precipitate crystals of the phenolic-hydroxyl-group-containing compound (A).

The purity of the phenolic-hydroxyl-group-containing compound (A), which is calculated from a GPC chart, is preferably 90% or more, more preferably 94% or more, and especially preferably 98% or more because the phenolic-hydroxyl-group-containing novolac resin having both excellent developability and heat resistance can be produced. The purity of the phenolic-hydroxyl-group-containing compound (A) can be determined from an area ratio in a gel permeation chromatography (GPC) chart.

In the present invention, measurement conditions in GPC are as follows.

[Measurement Conditions in GPC]

Measuring equipment: "HLC-8220 GPC" manufactured by Tosoh Corporation

Columns: "Shodex KF802" (8.0 mm φ×300 mm) manufactured by Showa Denko K.K.
+"Shodex KF802" (8.0 mm φ×300 mm) manufactured by Showa Denko K.K.
+"Shodex KF803" (8.0 mm φ×300 mm) manufactured by Showa Denko K.K.
+"Shodex KF804" (8.0 mm φ×300 mm) manufactured by Showa Denko K.K.

Column temperature: 40° C.
Detector: RI (differential refractometer)
Data processing: "GPC-8020 model II version 4.30" manufactured by Tosoh Corporation
Eluent: tetrahydrofuran
Flow rate: 1.0 ml/min
Sample: prepared by filtering a 0.5-mass % tetrahydrofuran solution in terms of resin solid content through a microfilter
Injection volume: 0.1 ml
Standard sample: monodisperse polystyrene described below (Standard samples: monodisperse polystyrene)
"A-500" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation Examples of the poor solvent (S1) used for purifying the phenolic-hydroxyl-group-containing compound (A) include water; monoalcohols such as methanol, ethanol, propanol, and ethoxyethanol; aliphatic hydrocarbons such as n-hexane, n-heptane, n-octane, and cyclohexane; and aromatic hydrocarbons such as toluene and xylene. These solvents may be used alone or in combination. Among these, water, methanol, and ethoxyethanol are preferred because they well serve to dissolve the acid catalyst.

Examples of the solvent (S2) include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxaene and 1,4-dioxane; glycol esters such as ethylene glycol acetate; and ketones such as acetone, methyl ethyl ketone, and methyl isobutyl ketone. These solvents may be used alone or in combination. In particular, when water or monoalcohol is used as the poor solvent (S1), acetone is preferably used as the solvent (S2).

The phenolic-hydroxyl-group-containing compound (B) is represented by Structural Formula (2)

[Chem. 14]

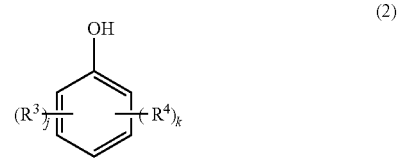

(2)

[where $R^3$ is an aliphatic hydrocarbon group having 4 to 20 carbon atoms; j is an integer from 1 to 3; $R^4$ is each independently a hydrogen atom, an alkyl group having 1 to 3 carbon atoms, an alkoxy group, an aryl group, an aralkyl group, or a halogen atom; k is an integer from 0 to (5-j)]. In production of the phenolic-hydroxyl-group-containing novolac resin of the present invention, the phenolic-hydroxyl-group-containing compound (B) that is to be used may be one of compounds represented by Structural Formula (2) or a combination of two or more thereof.

$R^3$ in Structural Formula (2) is an aliphatic hydrocarbon group having 4 to 20 carbon atoms and may be linear, branched, alicyclic, or unsaturated. Specific examples thereof include a butyl group, a pentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, and structural isomers thereof. Among these, aliphatic hydrocarbon groups having 8 to 16 carbon atoms, such as an octyl group, a nonyl group, a decyl group, an undecyl group, a dodecyl group, a tridecyl group, a tetradecyl group, a pentadecyl group, a hexadecyl group, and structural isomers thereof, are preferred because they enable production of a phenolic-hydroxyl-group-containing novolac resin having well-balanced developability, heat resistance, and conformability to substrates.

$R^4$ in Structural Formula (2) is each independently an alkyl group having 1 to 3 carbon atoms, an alkoxy group, an aryl group, an aralkyl group, or a halogen atom. Examples of the alkyl group include a methyl group, an ethyl group, and a propyl group. Examples of the alkoxy group include a methoxy group, an ethoxy group, a propyloxy group, a butoxy group, a pentyloxy group, a hexyloxy group, and a cyclohexyloxy group. Examples of the aryl group include a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group. Examples of the aralkyl group include a phenylmethyl group, a hydroxyphenylmethyl group, a dihydroxyphenylmethyl group, a tolylmethyl group, a xylylmethyl group, a naphthylmethyl group, a hydroxynaphthylmethyl group, a dihydroxynaphthylmethyl group, a phenylethyl group, a hydroxyphenylethyl group, a dihydroxyphenylethyl group, a tolylethyl group, a xylylethyl group, a naphthylethyl group, a hydroxynaphthylethyl group, and a dihydroxynaphthylethyl group. Examples of the halogen atom include a fluorine atom, a chlorine atom, and a bromine atom.

Among these, $R^4$ is preferably a hydrogen atom because they enable production of a phenolic-hydroxyl-group-containing novolac resin having well-balanced developability, heat resistance, and conformability to substrates.

The aldehyde compound (C) may be any aldehyde compound provided that it enables formation of a novolac resin structure through the condensation reaction of the phenolichydroxyl-group-containing compound (A) with the phenolic-hydroxyl-group-containing compound (B). Examples thereof include formaldehyde, para-formaldehyde, 1,3,5-trioxane, acetaldehyde, propionaldehyde, tetraoxymethylene, polyoxymethylene, chloral, hexamethylenetetramine, furfural, glyoxal, n-butylaldehyde, caproaldehyde, allyaldehyde, crotonaldehyde, and acrolein. These may be used alone or in combination. Among these, formaldehyde is preferably used because it has an excellent reactivity. The formaldehyde may be used either in the form of formalin that is in the state of an aqueous solution or in the form of para-formaldehyde that is in the state of a solid. In the case where the formaldehyde is used in combination with another aldehyde compound, the content proportion of such another aldehyde compound is preferably from 0.05 to 1 mol per mole of the formaldehyde.

The phenolic-hydroxyl-group-containing novolac resin of the present invention can be produced through the reaction of the phenolic-hydroxyl-group-containing compound (A), phenolic-hydroxyl-group-containing compound (B), and aldehyde compound (C) that are each an essential component.

The phenolic-hydroxyl-group-containing compound (A) and the phenolic-hydroxyl-group-containing compound (B) are used at a molar ratio [(A):(B)] ranging preferably from 100:0.1 to 100:30, and more preferably from 100:0.5 to 100:20 because such a molar ratio enables production of a phenolic-hydroxyl-group-containing novolac resin having well-balanced developability, heat resistance, and conformability to substrates.

The phenolic-hydroxyl-group-containing novolac resin of the present invention contains the phenolic-hydroxyl-group-containing compound (A) and the phenolic-hydroxyl-group-containing compound (B) as essential phenolic-hydroxyl-group-containing compound components for forming the structure of a novolac resin; however, another phenolic-hydroxyl-group-containing compound may be optionally used in combination. Examples of such another phenolic-hydroxyl-group-containing compound include alkylphenols such as phenol, cresol, and xylenol; alkoxy phenols such as methoxyphenol and ethoxyphenol; and resorcin, naphthol, and dihydroxynaphthalene. These compounds may be used alone or in combination. In the case where such another phenolic-hydroxyl-group-containing compound is used, the amount thereof is preferably 20 mass % or less relative to the total mass of the phenolic-hydroxyl-group-containing compound (A), the phenolic-hydroxyl-group-containing compound (B), and another phenolic-hydroxyl-group-containing compound because well-balanced developability, heat resistance, and conformability to substrates, which are effects of the present invention, are sufficiently produced.

In terms of the reaction molar ratio of the aldehyde compound (C) to the phenolic-hydroxyl-group-containing compound components in production of the phenolic-hydroxyl-group-containing novolac resin of the present invention, the aldehyde compound (C) is preferably 0.51.2 mol, and more preferably from 0.6 to 0.9 mol relative to 1 mol of the total of the phenolic-hydroxyl-group-containing compounds because such a reaction molar ratio contributes to a reduction in an unnecessary increase in molecular weight (gelation) and enables production of a phenolic-hydroxyl-group-containing novolac resin having a proper molecular weight for a resist material.

Examples of the acid catalyst used in the reaction of the phenolic-hydroxyl-group-containing compound components with the aldehyde compound (C) include acetic acid, oxalic acid, sulfuric acid, hydrochloric acid, phenolsulfonic acid, para-toluenesulfonic acid, zinc acetate, and manganese acetate. These acid catalysts may be used alone or in combination. Among these, sulfuric acid and para-toluenesulfonic acid are preferred because they are excellent in catalytic activity.

The reaction of the phenolic-hydroxyl-group-containing compound components with the aldehyde compound (C) may be optionally performed in an organic solvent. Examples of the solvent that is to be used include monoalcohols such as methanol, ethanol, and propanol; polyols such as ethylene glycol, 1,2-propanediol, 1,3-propanediol, 1,4-butanediol, 1,5-pentanediol, 1,6-hexanediol, 1,7-heptanediol, 1,8-octanediol, 1,9-nonanediol, trimethylene glycol, diethylene glycol, polyethylene glycol, and glycerin; glycol ethers such as 2-ethoxyethanol, ethylene glycol monomethyl ether, ethylene glycol monoethyl ether, ethylene glycol monopropyl ether, ethylene glycol monobutyl ether, ethylene glycol monopentyl ether, ethylene glycol dimethyl ether, ethylene glycol ethyl methyl ether, and ethylene glycol monophenyl ether; cyclic ethers such as 1,3-dioxaene, 1,4-dioxane, and tetrahydrofuran; glycol esters such as ethylene glycol acetate; and ketones such as acetone, methyl ethyl ketone, and methyl isobutyl ketone. These solvents may be used alone or in the form of a mixed solvent of two or more. Among these, 2-ethoxyethanol is preferred because the phenolic-hydroxyl-group-containing novolac resin that is to be produced has an excellent solubility.

The reaction of the phenolic-hydroxyl-group-containing compound components with the aldehyde compound (C) is, for example, performed at a temperature ranging from 60° C. to 140° C. for a duration of 0.5 to 100 hours.

After the termination of the reaction, water can be added to the reaction product for reprecipitation to obtain the intended phenolic-hydroxyl-group-containing novolac resin. The weight average molecular weight (Mw) of the phenolic-hydroxyl-group-containing novolac resin produced in this manner is preferably in the range of 10,000 to 30,000 because such a molecular weight enables the resin to have a well-balanced developability, heat resistance, and conformability to substrates and to be suitably used as a resist material. The polydispersity (Mw/Mn) of the phenolic-hydroxyl-group-containing novolac resin is preferably in the range of 3 to 10.

In the present invention, weight average molecular weight (Mw) and polydispersity (Mw/Mn) are measured by GPC under the following conditions.

[Measurement Conditions in GPC]

Measuring equipment: "HLC-8220 GPC" manufactured by Tosoh Corporation

Columns: "Shodex KF802" (8.0 mm $\phi \times 300$ mm) manufactured by Showa Denko K.K.+"Shodex KF802" (8.0 mm $\phi \times 300$ mm) manufactured by Showa Denko K.K.

+"Shodex KF803" (8.0 mm $\phi \times 300$ mm) manufactured by Showa Denko K.K.+"Shodex KF804" (8.0 mm $\phi \times 300$ mm) manufactured by Showa Denko K.K.

Column temperature: 40° C.

Detector: RI (differential refractometer)

Data processing: "GPC-8020 model II version 4.30" manufactured by Tosoh Corporation Eluent: tetrahydrofuran Flow rate: 1.0 mL/min Sample: prepared by filtering a 0.5-mass % tetrahydrofuran solution in terms of resin solid content through a microfilter (100 μl)

Standard sample: monodisperse polystyrene described below (Standard samples: monodisperse polystyrene)
"A-500" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation The phenolic-hydroxyl-group-containing novolac resin of the present invention may have any resin structure provided that it is a polycondensate of which the essential reactive components are the phenolic-hydroxyl-group-containing compound (A), the phenolic-hydroxyl-group-containing compound (B), and the aldehyde compound (C). Examples of the phenolic-hydroxyl-group-containing novolac resin include phenolic-hydroxyl-group-containing novolac resins each having repeating units that are a structural part (a) represented by Structural Formula (3)

[Chem. 15]

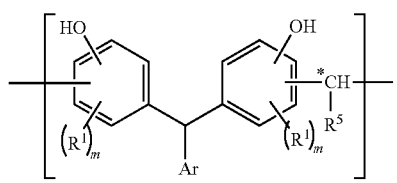

(3)

[where Ar is a structural part represented by Structural Formula (Ar-3) or (Ar-4)

[Chem. 16]

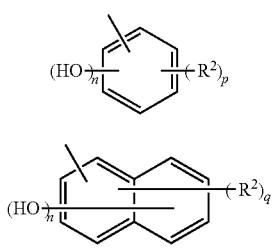

(Ar-3)

(Ar-4)

(where n in each formula is independently an integer from 0 to 2; p is an integer from 0 to 5; q is an integer from 0 to 7; and $R^2$ in each formula is independently a hydrogen atom, an alkyl group, an alkoxy group, an aryl group, an aralkyl group, a halogen atom, or a linking point that connects with the structural part represented by Structural Formula (3) or (4) via the carbon atom denoted by the symbol *);

$R^1$'s are each independently a hydrogen atom, an alkyl group, an alkoxy group, an aryl group, an aralkyl group, or a halogen atom; m's are each independently an integer from 0 to 4; and $R^5$ is a hydrogen atom, an alkyl group, or an aryl group] and a structural part (b) represented by Structural Formula (4)

[Chem. 17]

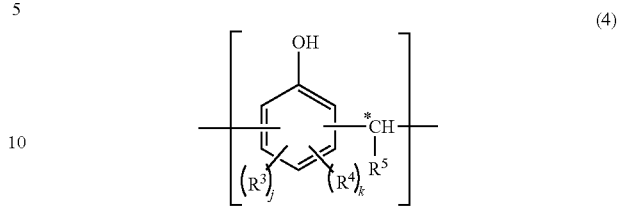

(4)

[where $R^3$ is an aliphatic hydrocarbon group having 4 to 20 carbon atoms; j is an integer from 1 to 3; $R^4$ is each independently a hydrogen atom, an alkyl group having 1 to 3 carbon atoms, an alkoxy group, an aryl group, an aralkyl group, a halogen atom, or a linking point that connects with the structural part represented by Structural Formula (3) or (4) via the carbon atom denoted by the symbol *; k is an integer from 0 to (5-j); and $R^5$ is a hydrogen atom, an alkyl group, or an aryl group].

In particular, the phenolic-hydroxyl-group-containing novolac resin is preferably a phenolic-hydroxyl-group-containing novolac resin having repeating units that are a structural part (a-1) represented by Structural Formula (3-1)

[Chem. 18]

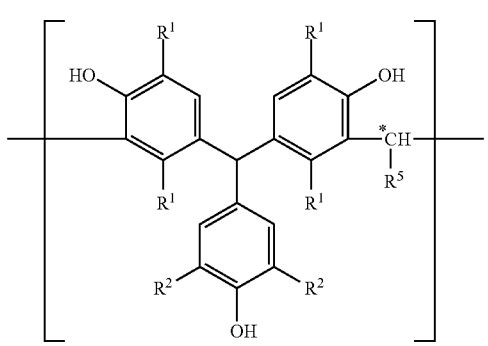

(3-1)

[where $R^1$'s are each independently a hydrogen atom, an alkyl group, an alkoxy group, an aryl group, an aralkyl group, or a halogen atom; $R^5$ is a hydrogen atom, an alkyl group, or an aryl group; $R^2$'s are each independently a hydrogen atom or a linking point that connects with the structural part represented by Structural Formula (3-1) or (4-1) via the carbon atom denoted by the symbol *] and a structural part (b-1) represented by Structural Formula (4-1)

[Chem. 19]

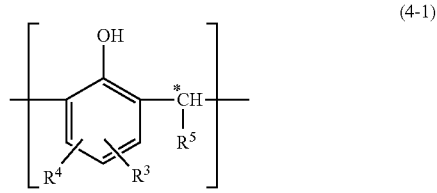

(4-1)

[where $R^3$ is an aliphatic hydrocarbon group having 4 to 20 carbon atoms; $R^5$ is a hydrogen atom, an alkyl group, or an aryl group; and $R^4$ is a hydrogen atom or a linking point that connects with the structural part represented by Structural Formula (3-1) or (4-1) via the carbon atom denoted by the symbol *].

The molar ratio [(a-1):(b-1)] of the structural part (a-1) to the structural part (b-1) in the resin is preferably in the range of 100:0.1 to 100:30, and more preferably 100:0.5 to 100:20 because such a molar ratio enables production of a phenolic-hydroxyl-group-containing novolac resin having well-balanced developability, heat resistance, and conformability to substrates.

The phenolic-hydroxyl-group-containing novolac resin of the present invention, which has been described above in detail, is excellent in solubility in general organic solvents and in resistance to thermal decomposition and therefore can be used in adhesives, coating materials, photoresists, and a variety of electric and electronic members such as printed circuit boards. The phenolic-hydroxyl-group-containing novolac resin of the present invention is excellent in alkali-solubility as well and therefore particularly suitably used in resists; hence, the resin can be a resist material having excellent photosensitivity and resolution. The phenolic-hydroxyl-group-containing novolac resin of the present invention is excellent not only in developability but also in heat resistance and flexibility and can be allowed to react with a curing agent into a cured product having a high stiffness; thus, the resin can be properly used in thick films, resist underlayer films, and permanent resist films. In formation of a thick film, for instance, a resist film of the phenolic-hydroxyl-group-containing novolac resin enables formation of a sufficiently accurate resist pattern and is highly flexible and hard to be broken as in general resist films. In the case where the phenolic-hydroxyl-group-containing novolac resin is used in underlayer films or permanent films, the resin is excellent in conformability to substrates and less likely to suffer from degradation and a change in quality due to heating in production of semiconductor devices.

The photosensitive composition of the present invention contains the phenolic-hydroxyl-group-containing novolac resin of the present invention and a photosensitizer as essential components. The photosensitive composition of the present invention may contain another resin (X) in addition to the phenolic-hydroxyl-group-containing novolac resin of the present invention. Such another resin (X) can be any resin provided that it is soluble in an alkaline developer or used in combination with an additive, such as an acid generator, to become soluble in an alkaline developer.

Example of such another resin (X) include phenolic resins (X-1) other than the phenolic-hydroxyl-group-containing novolac resin; homopolymers or copolymers (X-2) of hydroxyl-group-containing styrene compounds, such as p-hydroxystyrene and p-(1,1,1,3,3,3-hexafluoro-2-hydroxypropyl)styrene; products (X-3) obtained by modifying the hydroxyl group of the (X-1) or the (X-2) with an acid-decomposable group such as a t-butoxycarbonyl group or a benzyloxycarbonyl group; homopolymers or copolymers (X-4) of (meth)acrylic acid; and alternating polymers (X-5) of a alicyclic polymerizable monomer, such as a norbornene compound or a tetracyclododecene compound, with maleic anhydride or maleimide.

Examples of the phenolic resin (X-1) include phenolic resins such as phenolic novolac resins, cresol novolac resins, naphthol novolac resins, co-condensation novolac resins containing a variety of phenolic compounds, aromatic-hydrocarbon-formaldehyde-resin-modified phenolic resins, dicyclopentadiene-phenol-added resins, phenol aralkyl resins (Xylok resins), naphthol aralkyl resins, trimethylol methane resins, tetraphenylol ethane resins, biphenyl-modified phenolic resins (polyhydric phenolic compounds in which phenol nuclei are connected via a bismethylene group), biphenyl-modified naphthol resins (polyhydric naphthol compounds in which phenol nuclei are connected via a bismethylene group), aminotriazine-modified phenolic resins (polyhydric phenolic compounds in which phenol nuclei are connected via, for instance, melamine or benzoguanamine), and alkoxy-group-containing aromatic-ring-modified novolac resins (polyhydric phenolic compounds in which a phenol nucleus and an alkoxy-group-containing aromatic ring are connected via formaldehyde).

Among the phenolic resins (X), cresol novolac resins or co-condensation novolac resins of cresol with other phenolic compounds are preferred because they enable production of a photosensitive resin composition having high sensitivity and excellent heat resistance. Specifically, the cresol novolac resins or co-condensation novolac resins of cresol with other phenolic compounds are novolac resins produced by using at least one cresol selected from the group consisting of o-cresol, m-cresol, and p-cresol and an aldehyde compound as essential raw materials and appropriately using another phenolic compound in combination.

Examples of the phenolic compounds other than cresols include phenol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as p-phenylphenol, aminophenol, nitrophenol, dinitrophenol, and trinitrophenol; condensed polycyclic phenols such as 1-naphthol and 2-naphthol; and polyphenols such as resorcinol, alkyl resorcinol, pyrogallol, catechol, alkyl catechol, hydroquinone, alkyl hydroquinone, phloroglucin, bisphenol A, bisphenol F, bisphenol S, and dihydroxynaphthalene. These other phenolic compounds may be used alone or in combination. In the case of using such other phenolic compounds, the amount of the phenolic compounds is preferably in the range of 0.05 to 1 mol relative to 1 mol of the total of the cresol raw materials.

Examples of the aldehyde compound include formaldehyde, para-formaldehyde, trioxane, acetaldehyde, propionaldehyde, polyoxymethylene, chloral, hexamethylenetetramine, furfural, glyoxal, n-butyraldehyde, caproaldehyde, allyl aldehyde, benzaldehyde, crotonaldehyde, acrolein, tetraoxymethylene, phenyl acetaldehyde, o-tolualdehyde, and salicylaldehyde. These aldehyde compounds may be used alone or in combination. Among these, formaldehyde is preferred because it has an excellent reactivity, and formaldehyde and other aldehyde compounds may be used in combination. In the case where formaldehyde and other aldehyde compounds are used in combination, the amount of other aldehyde compounds is preferably in the range of 0.05 to 1 mol relative to 1 mol of formaldehyde.

In the reaction of the phenolic compound with the aldehyde compound for producing the novolac resin, the amount of the aldehyde compound is preferably in the range of 0.3 to 1.6 mol, and more preferably 0.5 to 1.3 relative to 1 mole of the phenolic compound because such an amount enables production of a photosensitive resin composition having excellent sensitivity and heat resistance.

The reaction of the phenolic compound with the aldehyde compound is performed at a temperature ranging from 60 to 140° C. in the presence of an acid catalyst, and then, for example, a process for removing water and a residual monomer under reduced pressure is performed. Examples of the acid catalyst to be used include oxalic acid, sulfuric acid, hydrochloric acid, phenolsulfonic acid, para-toluenesulfonic acid, zinc acetate, and manganese acetate; and these may be used alone or in combination. Among these, oxalic acid is preferred because it has an excellent catalytic activity.

Among the cresol novolac resins or co-condensation novolac resins of cresol with other phenolic compounds detailed above, a cresol novolac resin produced by using meta-cresol alone or a cresol novolac resin produced by using meta-cresol and para-cresol in combination is preferred. In the latter, the reaction molar ratio [meta-cresol/para-cresol] of meta-cresol to para-cresol is preferably in the range of 10/0 to 2/8, and more preferably 7/3 to 2/8 because such a ratio enables production of a photosensitive resin composition having well-balanced sensitivity and heat resistance.

In the case where other resins (X) are used, the content percentages of the phenolic-hydroxyl-group-containing novolac resin of the present invention and other resins (X) can be arbitrarily adjusted depending on the intended application thereof. For example, since the phenolic-hydroxyl-group-containing novolac resin of the present invention has excellent photosensitivity, excellent resolution, and excellent heat resistance when it is combined with a photosensitizer, a photosensitive composition containing the phenolic-hydroxyl-group-containing novolac resin as the main component is optimally used in resists. In this case, the amount of the phenolic-hydroxyl-group-containing novolac resin of the present invention is preferably 60 mass % or more, and more preferably 80 mass % or more in the total resin components because such an amount enables production of a curable composition having a high photosensitivity, excellent resolution, and excellent heat resistance.

Since the phenolic-hydroxyl-group-containing novolac resin of the present invention has an excellent photosensitivity, this resin can be used as a sensitivity improver. In this case, the amount of the phenolic-hydroxyl-group-containing novolac resin of the present invention is preferably in the range of 3 to 80 parts by mass relative to 100 parts by mass of other resins (X).

Examples of the photosensitizer include compounds having a quinonediazide group. Specific examples of the compounds having a quinonediazide group include complete ester compounds, partial ester compounds, amidated products, and partially amidated products of an aromatic (poly)hydroxyl compound with sulfonic acid having a quinonediazide group, such as naphthoquinone-1,2-diazido-5-sulfonic acid, naphthoquinone-1,2-diazido-4-sulfonic acid, or orthoanthraquinonediazidosulfonic acid.

Examples of the aromatic (poly)hydroxyl compound to be used include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis(2,4-dihydroxyphenyl)methane, bis(2,3,4-trihydroxyphenyl)methane, 2-(4-hydroxyphenyl)-2-(4'-hydroxyphenyl)propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

tris(hydroxyphenyl)methane compounds, such as tris(4-hydroxyphenyl)methane, bis(4-hydroxy-3,5-dimethylphenyl)-4-hydroxyphenyl methane, bis(4-hydroxy-2,5-dimethylphenyl)-4-hydroxyphenyl methane, bis(4-hydroxy-3,5-dimethylphenyl)-2-hydroxyphenyl methane, bis(4-hydroxy-2,5-dimethylphenyl)-2-hydroxyphenyl methane, bis(4-hydroxy-2,5-dimethylphenyl)-3,4-dihydroxyphenyl methane, and bis(4-hydroxy-3,5-dimethylphenyl)-3,4-dihydroxyphenyl methane, and methyl-substituted products thereof; and bis(cyclohexylhydroxyphenyl)(hydroxyphenyl)methane compounds, such as bis(3-cyclohexyl-4-hydroxyphenyl)-3-hydroxyphenyl methane, bis(3-cyclohexyl-4-hydroxyphenyl)-2-hydroxyphenyl methane, bis(3-cyclohexyl-4-hydroxyphenyl)-4-hydroxyphenyl methane, bis(5-cyclohexyl-4-hydroxy-2-methylphenyl)-2-hydroxyphenyl methane, bis(5-cyclohexyl-4-hydroxy-2-methylphenyl)-3-hydroxyphenyl methane, bis(5-cyclohexyl-4-hydroxy-2-methylphenyl)-4-hydroxyphenyl methane, bis(3-cyclohexyl-2-hydroxyphenyl)-3-hydroxyphenyl methane, bis(5-cyclohexyl-4-hydroxy-3-methylphenyl)-4-hydroxyphenyl methane, bis(5-cyclohexyl-4-hydroxy-3-methylphenyl)-3-hydroxyphenyl methane, bis(5-cyclohexyl-4-hydroxy-3-methylphenyl)-2-hydroxyphenyl methane, bis(3-cyclohexyl-2-hydroxyphenyl)-4-hydroxyphenyl methane, bis(3-cyclohexyl-2-hydroxyphenyl)-2-hydroxyphenyl methane, bis(5-cyclohexyl-2-hydroxy-4-methylphenyl)-2-hydroxyphenyl methane, and bis(5-cyclohexyl-2-hydroxy-4-methylphenyl)-4-hydroxyphenyl methane, and methyl-substituted products thereof. These photosensitizers may be used alone or in combination.

The amount of the photosensitizer in the photosensitive composition of the present invention is preferably in the range of 5 to 50 parts by mass relative to 100 parts by mass of the whole resin solid content of the photosensitive composition because such an amount enables the photosensitive composition to have an excellent photosensitivity.

The photosensitive composition of the present invention may contain a surfactant in order to improve film formability and the adhesion of patterns and to reduce defective development in application to resists. Examples of the surfactant to be used include nonionic surfactants such as polyoxyethylene alkyl ether compounds including polyoxyethylene lauryl ether, polyoxyethylene stearyl ether, polyoxyethylene cetyl ether, and polyoxyethylene oleyl ether, polyoxyethylene alkyl allyl ether compounds including polyoxyethylene octylphenol ether and polyoxyethylene nonylphenol ether, polyoxyethylene-polyoxypropylene block copolymers, sorbitan fatty acid ester compounds including sorbitan monolaurate, sorbitan monopalmitate, sorbitan monostearate, sorbitan monooleate, sorbitan trioleate, and sorbitan tristearate, polyoxyethylene sorbitan fatty acid ester compounds including polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine-based surfactants each having a fluorine atom in its molecular structure, such as a copolymer of a polymerizable monomer having a fluoroaliphatic group with [poly(oxyalkylene)](meth)acrylate; and silicone surfactants each having a silicone structural moiety in its molecular structure. These surfactants may be used alone or in combination.

The amount of the surfactant is preferably in the range of 0.001 to 2 parts by mass relative to 100 parts by mass of the total resin solid content in the photosensitive composition of the present invention.

In the case where the photosensitive composition of the present invention is used in photoresists, the phenolic-hydroxyl-group-containing novolac resin of the present invention, the photosensitizer, and optionally a variety of additives such as other phenolic resins (X), a surfactant, a dye, a filler, a crosslinking agent, and a dissolution accelerator are added and dissolved in an organic solvent to produce a resist composition. The resist composition may be directly used as a positive resist solution; alternatively, the resist composition may be applied in the form of a film and then subjected to removal of the solvent to form a positive resist film. Examples of the support film of such a resist film include synthetic resin films such as polyethylene, polypropylene, polycarbonate, and polyethylene terephthalate. The support film may be a single layer film or a laminated film. The surface of the support film may be a surface subjected to a corona treatment or coated with a release agent.

The organic solvent used in the resist composition of the present invention is not particularly limited. Examples thereof include alkylene glycol monoalkyl ethers such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; akylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These may be used alone or in combination.

The resist composition of the present invention can be produced by preparing the above-described components and mixing them by use of a mixer or another device. In addition, in the case where the resin composition for photoresists contains a filler or a pigment, a dispersing apparatus, such as a dissolver, a homogenizer, or a three-roll mill, can be used for dispersion or mixing to produce the resin composition.

Photolithography in which the resist composition of the present invention is used, for example, involves applying the resist composition onto an object on which silicon substrate photolithography is to be performed and prebaking it at a temperature ranging from 60 to 150° C. The resist composition may be applied by any of techniques including spin coating, roll coating, flow coating, dip coating, spray coating, and doctor blade coating. Then, a resist pattern is formed; since the resist composition of the present invention is a positive type, the intended resist pattern is exposed through a predetermined mask, and the exposed part is dissolved with an alkaline developer, thereby forming a resist pattern. The resist composition of the present invention gives the exposed part high alkali-solubility and also gives non-exposed part high resistance to alkali-solubility, and thus a resist pattern having an excellent resolution can be formed.

The curable composition of the present invention contains the phenolic-hydroxyl-group-containing novolac resin of the present invention and a curing agent as essential components. The curable composition of the present invention may contain other resins (Y) in addition to the phenolic-hydroxyl-group-containing resin of the present invention. Examples of such other resins (Y) to be used include a variety of novolac resins; addition polymerization resins of alicyclic diene compounds, such as dicyclopentadiene, with phenolic compounds; modified novolac resins of phenolic-hydroxyl-group-containing compounds with alkoxy-group-containing aromatic compounds; phenol aralkyl resins (Xylok resins); naphthol aralkyl resins; trimethylol methane resins; tetraphenylol ethane resins; biphenyl-modified phenolic resins; biphenyl-modified naphthol resins; aminotriazine-modified phenolic resins; and a variety of vinyl polymers.

Specific examples of the above-mentioned variety of novolac resins include alkylphenols such as phenolenol, cresol, and xylenol; bisphenols such as phenylphenol, resorcinol, biphenyl, bisphenol A, and bisphenol F; and polymers produced through the reaction of compounds containing a phenolic hydroxyl group, such as naphthol or dihydroxynaphthalene, with aldehyde compounds under acid catalyst conditions.

Examples of the above-mentioned variety of vinyl polymers include homopolymers or copolymers of vinyl compounds such as polyhydroxystyrene, polystyrene, polyvinylnaphthalene, polyvinylanthracene, polyvinylcarbazole, polyindene, polyacenaphthylene, polynorbornene, polycyclodecene, polytetracyclododecene, polynortricyclene, and poly(meth)acrylate.

In the case where such other resins are used, the amounts of the phenolic-hydroxyl-group-containing novolac resin of the present invention and other resins (Y) can be arbitrarily determined depending on the application; the amount of other resins (Y) is preferably in the range of 0.5 to 100 parts by mass relative to 100 parts by mass of the phenolic-hydroxyl-group-containing novolac resin of the present invention because excellent dry etching resistance and resistance to thermal decomposition, which are effects of the present invention, can be more clearly produced.

Examples of the curing agent used in the present invention include melamine compounds substituted with at least one group selected from a methylol group, an alkoxymethyl group, and an acyloxymethyl group; guanamine compounds; glycoluril compounds; urea compounds; resole resins; epoxy compounds; isocyanate compounds; azide compounds; compounds containing a double bond such as an alkenyl ether group; acid anhydrides; and oxazoline compounds.

Examples of the melamine compounds include hexamethylolmelamine, hexamethoxymethylmelamine, compounds in which 1 to 6 methylol groups in hexamethylolmelamine have been methoxymethylated, hexamethoxyethylmelamine, hexaacyloxymethylmelamine, and compounds in which 1 to 6 methylol groups in hexamethylolmelamine have been acyloxymethylated.

Examples of the guanamine compounds include tetramethylolguanamine, tetramethoxymethylguanamine, tetraethoxymethylbenzoguanamine, compounds in which 1 to 4 methylol groups in tetramethylolguanamine have been methoxymethylated, tetramethoxyethylguanamine, tetraacyloxyguanamine, and compounds in which 1 to 4 methylol groups in tetramethylolguanamine have been acyloxymethylated.

Examples of the glycoluril compounds include 1,3,4,6-tetrakis(methoxymethyl)glycoluril, 1,3,4,6-tetrakis(butoxymethyl)glycoluril, and 1,3,4,6-tetrakis(hydroxymethyl)glycoluril.

Examples of the urea compounds include 1,3-bis(hydroxymethyl)urea, 1,1,3,3-tetrakis(butoxymethyl)urea, and 1,1,3,3-tetrakis(methoxymethyl)urea.

Examples of the resole resins include alkylphenols such as phenol, cresol, and xylenol; bisphenols such as phenylphenol, resorcinol, biphenyl, bisphenol A, and bisphenol F; and polymers produced through the reaction of compounds containing a phenolic hydroxyl group, such as naphthol or dihydroxynaphthalene, with aldehyde compounds under alkali catalyst conditions.

Examples of the epoxy compounds include diglycidyloxynaphthalene, phenol novolac epoxy resins, cresol novolac epoxy resins, naphthol novolac epoxy resins, naphthol-phenol co-condensed novolac epoxy resins, naphthol-cresol co-condensed novolac epoxy resins, phenol aralkyl epoxy resins, naphthol aralkyl epoxy resins, 1,1-bis(2,7-diglycidyloxy-1-naphthyl)alkane, naphthylene ether epoxy resins, triphenylmethane epoxy resins, dicyclopentadiene-phenol addition-reaction-type epoxy resins, phosphorus-containing epoxy resins, and polyglycidyl ethers of co-condensate of phenolic-hydroxyl-group-containing compounds with alkoxy-group-containing aromatic compounds.

Examples of the isocyanate compounds include tolylene diisocyanate, diphenylmethane diisocyanate, hexamethylene diisocyanate, and cyclohexane diisocyanate.

Examples of the azide compounds include 1,1'-biphenyl-4,4'-bisazide, 4,4'-methylidenebisazide, and 4,4'-oxybisazide. [0116]

Examples of the compounds containing a double bond such as an alkenyl ether group include ethyleneglycol divinyl ether, triethyleneglycol divinyl ether, 1,2-propanediol divinyl ether, 1,4-butanediol divinyl ether, tetramethyleneglycol divinyl ether, neopentylglycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of the acid anhydrides include aromatic acid anhydrides, such as phthalic anhydride, trimellitic anhydride, pyromellitic anhydride, 3,3',4,4'-benzophenonetetracarboxylic dianhydride, biphenyltetracarboxylic dianhydride, 4,4'-(isopropylidene)diphthalic anhydride, and 4,4'-(hexafluoro isopropylidene)diphthalic anhydride, and alicyclic carboxylic acid anhydrides such as tetrahydrophthalic anhydride, methyltetrahydrophthalic anhydride, hexahydrophthalic anhydride, methylhexahydrophthalic anhydride, endomethylene tetrahydrophthalic anhydride, dodecenylsuccinic anhydride, and trialkyltetrahydrophthalic anhydride.

Among these, glycoluril compounds, urea compounds, and resole resins are preferred because they enable production of a curable composition which has excellent curing properties and of which the curing product has an excellent heat resistance, and glycoluril compounds are especially preferred.

The amount of the curing agent in the curable composition of the present invention is preferably in the range of 0.5 to 50 parts by mass relative to 100 parts by mass of the total of the phenolic-hydroxyl-group-containing novolac resin of the present invention and other resins (Y) because such an amount enables production of a composition having excellent curing properties.

In the case where the curable composition of the present invention is used in resist underlayer films (BARC films), the phenolic-hydroxyl-group-containing novolac resin of the present invention, the curing agent, and optionally a variety of additives, such as other resins (Y), a surfactant, a dye, a filler, a crosslinking agent, and a dissolution accelerator, are added and dissolved in an organic solvent to produce a composition for resist underlayer films.

The organic solvent used in the composition for resist underlayer films is not particularly limited. Examples thereof include alkylene glycol monoalkyl ethers such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; akylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate. These solvents may be used alone or in combination.

The composition for resist underlayer films can be produced by preparing the above-described components and mixing them by use of a mixer or another device. In addition, in the case where the composition for resist underlayer films contains a filler or a pigment, a dispersing apparatus, such as a dissolver, a homogenizer, or a three-roll mill, can be used for dispersion or mixing to produce the resin composition.

In formation of a resist underlayer film of the composition for resist underlayer films, for example, the composition for resist underlayer films is applied onto an object on which photolithography is to be performed, such as a silicon substrate, dried at a temperature ranging from 100 to 200° C., and thermally cured at a temperature ranging from 250 to 400° C., thereby forming a resist underlayer film. Then, a resist pattern is formed on the underlayer film through a general photolithographic process, and the resist pattern is subjected to dry etching with a halogen-involving plasma gas or another material; in this manner, a resist pattern based on a multilayer resist method can be formed.

In the case where the curable composition of the present invention is used in permanent resist films, the phenolic-hydroxyl-group-containing novolac resin of the present invention, the curing agent, and optionally a variety of additives, such as other resins (Y), a surfactant, a dye, a filler, a crosslinking agent, and a dissolution accelerator, are added and dissolved in an organic solvent to produce a composition for permanent resist films. In this case, examples of the organic solvent include the same as the organic solvent used in the composition for resist underlayer films.

In an example of photolithography in which the composition for permanent resist films is used, resin components and additive components are dissolved or dispersed in an organic solvent, applied onto an object on which silicon substrate photolithography is to be performed, and prebaked at a temperature ranging from 60 to 150° C. The solution may be applied by any of techniques including spin coating, roll coating, flow coating, dip coating, spray coating, and doctor blade coating. Then, a resist pattern is formed; in the case where the composition for permanent resist films is a positive type, a resist pattern is formed by exposing the intended resist pattern through a predetermined mask and dissolving the exposed part in an alkaline developer.

Permanent films formed of the composition for permanent resist films can be suitably used, for example, in a solder resist, a packaging material, an underfill material, an adhesive layer for the package of a circuit element, or an adhesive layer between an integrated circuit element and a circuit board in the field of semiconductor devices and in a film for protecting a thin film transistor, a film for protecting a liquid crystal color filter, a black matrix, and a spacer in the field of thin display devices such as LCDs and OELDs.

EXAMPLES

The present invention will now be described further in detail with reference to specific examples. The number average molecular weights (Mn), weight average molecular weights (Mw), and polydispersities (Mw/Mn) of synthesized resins were measured by GPC under the following conditions.

[Measurement Conditions in GPC]
Measuring equipment: "HLC-8220 GPC" manufactured by Tosoh Corporation
Columns: "Shodex KF802" (8.0 mm φ×300 mm) manufactured by Showa Denko K.K.+"Shodex KF802" (8.0 mm φ×300 mm) manufactured by Showa Denko K.K.
+"Shodex KF803" (8.0 mm φ×300 mm) manufactured by Showa Denko K.K.+"Shodex KF804" (8.0 mm φ×300 mm) manufactured by Showa Denko K.K.
Column temperature: 40° C.
Detector: RI (differential refractometer)
Data processing: "GPC-8020 model II version 4.30" manufactured by Tosoh Corporation
Eluent: tetrahydrofuran
Flow rate: 1.0 mL/min
Sample: prepared by filtering a 0.5-mass % tetrahydrofuran solution in terms of resin solid content through a microfilter
Injection volume: 0.1 mL
Standard sample: monodisperse polystyrene described below
(Standard samples: monodisperse polystyrene)
"A-500" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation In measurement of a $^{13}$C-NMR spectrum, "AL-400" manufactured by JEOL Ltd. was used, and a solution of a sample in DMSO-$d_6$ was used for a structural analysis. The conditions of the measurement of a $^{13}$C-NMR spectrum were as follows.

[Conditions of Measurement of $^{13}$C-NMR Spectrum]
Measurement mode: SGNNE (1H complete decoupling with elimination of NOE)
Pulse angle: 45° C. pulse
Concentration of sample: 30 wt %
Number of integration: 10000 times Production Example 1

Production of Phenolic-hydroxyl-Group-Containing Compound (A-1)

Figure 2:
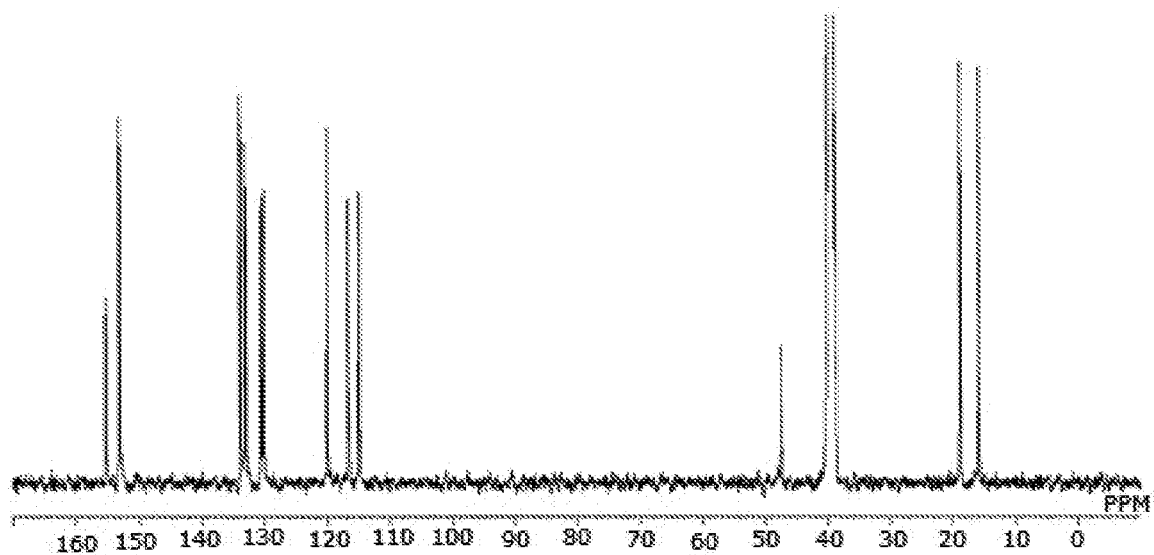
FIG. 2 is a ¹³C-NMR chart of the phenolic-hydroxyl-group-containing compound (A-1) produced in Production Example 1.

Into a 2000-ml four-neck flask equipped with a cooling pipe, 293.2 g (2.4 mol) of 2,5-xylenol and 122 g (1 mol) of 4-hydroxybenzaldehyde were put. The content was dissolved in 500 ml of 2-ethoxyethanol. Then, 10 ml of sulfuric acid was added thereto under cooling in an ice bath, and the resulting solution is heated to 100° C. with a mantle heater. The solution was subjected to a reaction for two hours under stirring. After the reaction, water was added to the resulting solution to reprecipitate a crude product. The crude product was re-dissolved in acetone and then reprecipitated in water. The precipitate was subsequently separated by filtration and dried under reduced pressure to yield 213 g of a phenolic-hydroxyl-group-containing compound (A-1) of white crystal. The compound was subjected to the $^{13}$C-NMR analysis, and production of a compound represented by the below structural formula was determined. The purity thereof calculated from a GPC chart was 98.2%. FIG. 1 illustrates the GPC chart of the phenolic-hydroxyl-group-containing compound (A-1), and FIG. 2 illustrates the $^{13}$C-NMR chart thereof.

[Chem. 20]

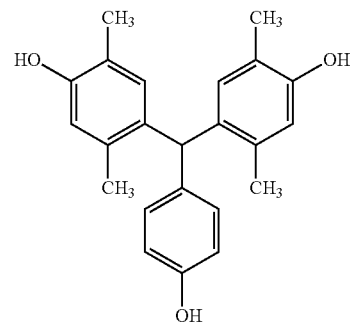

Example 1

Production of Phenolic-hydroxyl-Group-Containing Novolac Resin (1)

Figure 3:
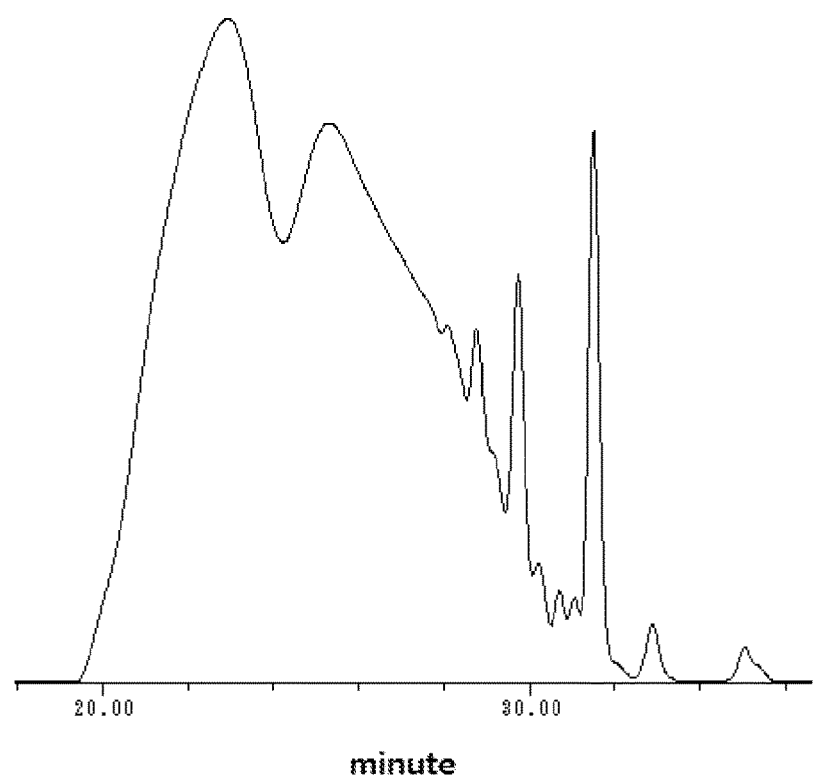
FIG. 3 is a GPC chart of a phenolic-hydroxyl-group-containing novolac resin (1) produced in Example 1.

Into a 300-ml four-neck flask equipped with a cooling pipe, 34.8 g (0.1 mol) of the phenolic-hydroxyl-group-containing compound (A-1) and 1.5 g (0.005 mol) of 3-pentadecylphenol were put. The content was dissolved in 15 ml of 2-ethoxyethanol and 15 ml of acetic acid. Then, 10 ml of sulfuric acid was added thereto under cooling in an ice bath, and 3.3 g (0.1 mol) of 92% paraformaldehyde was subsequently added thereto. The resulting solution was heated to 80° C. in an oil bath, and the solution was subjected to a reaction under heating and stirring for 10 hours. After the reaction, water was added to the resulting solution to reprecipitate a crude product. The crude product was re-dissolved in acetone and then reprecipitated in water. The precipitate was subsequently separated by filtration and dried under reduced pressure to yield 33.6 g of a phenolic-hydroxyl-group-containing novolac resin (1) of red powder. FIG. 3 illustrates the GPC chart of the phenolic-hydroxyl-group-containing novolac resin (1). The phenolic-hydroxyl-group-containing novolac resin (1) had a number average molecular weight (Mn) of 2,909, a weight average molecular weight (Mw) of 14,426, and polydispersity (Mw/Mn) of 4.96.

Example 2

Production of Phenolic-hydroxyl-Group-Containing Novolac Resin (2)

Figure 4:
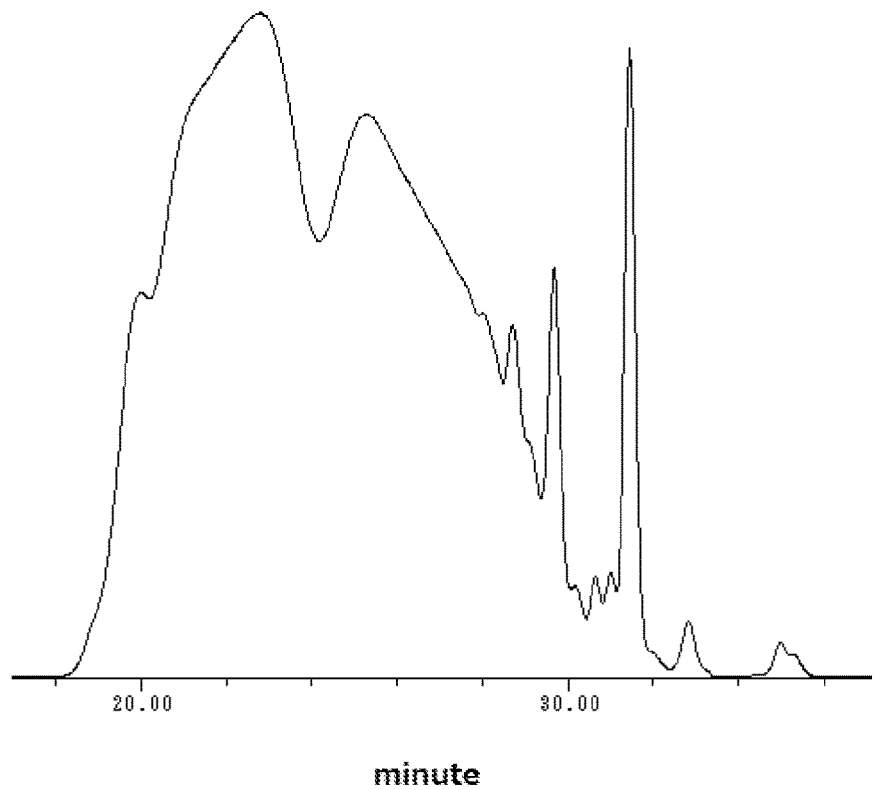
FIG. 4 is a GPC chart of a phenolic-hydroxyl-group-containing novolac resin (2) produced in Example 2.

Into a 300-ml four-neck flask equipped with a cooling pipe, 34.8 g (0.1 mol) of the phenolic-hydroxyl-group-containing compound (A-1) and 6.1 g (0.02 mol) of 3-pentadecylphenol were put. The content was dissolved in 15 ml of 2-ethoxyethanol and 15 ml of acetic acid. Then, 10 ml of sulfuric acid was added thereto under cooling in an ice bath, and 3.3 g (0.1 mol) of 92% paraformaldehyde was subsequently added thereto. The resulting solution was heated to 80° C. in an oil bath, and the solution was subjected to a reaction under heating and stirring for 10 hours. After the reaction, water was added to the resulting solution to reprecipitate a crude product. The crude product was re-dissolved in acetone and then reprecipitated in water. The precipitate was subsequently separated by filtration and dried under reduced pressure to yield 37.3 g of a phenolic-hydroxyl-group-containing novolac resin (2) of red powder. FIG. 4 illustrates the GPC chart of the phenolic-hydroxyl-group-containing novolac resin (2). The phenolic-hydroxyl-group-containing novolac resin (2) had a number average molecular weight (Mn) of 3,200, a weight average molecular weight (Mw) of 24,188, and polydispersity (Mw/Mn) of 7.56.

Example 3

Production of Phenolic-hydroxyl-Group-Containing Novolac Resin (3)

Figure 5:
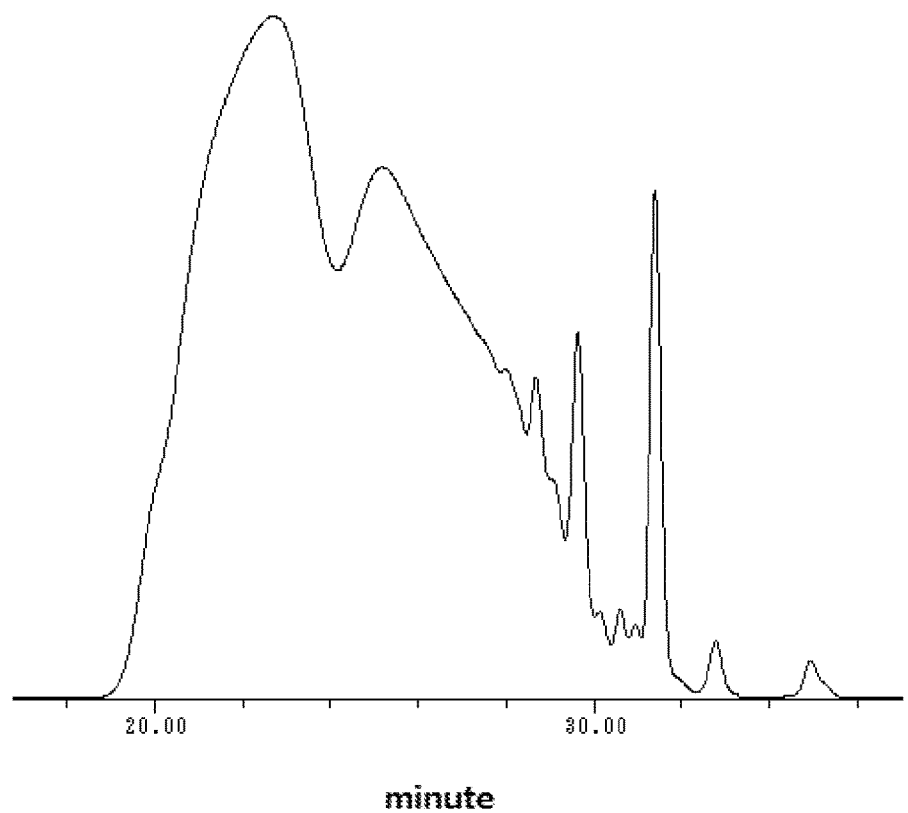
FIG. 5 is a GPC chart of a phenolic-hydroxyl-group-containing novolac resin (3) produced in Example 3.

Into a 300-ml four-neck flask equipped with a cooling pipe, 34.8 g (0.1 mol) of the phenolic-hydroxyl-group-containing compound (A-1) and 2.2 g (0.01 mol) of 4-nonylphenol were put. The content was dissolved in 15 ml of 2-ethoxyethanol and 15 ml of acetic acid. Then, 10 ml of sulfuric acid was added thereto under cooling in an ice bath, and 3.3 g (0.1 mol) of 92% paraformaldehyde was subsequently added thereto. The resulting solution was heated to 80° C. in an oil bath, and the solution was subjected to a reaction under heating and stirring for 10 hours. After the reaction, water was added to the resulting solution to reprecipitate a crude product. The crude product was re-dissolved in acetone and then reprecipitated in water. The precipitate was subsequently separated by filtration and dried under reduced pressure to yield 35.1 g of a phenolic-hydroxyl-group-containing novolac resin (3) of red powder. FIG. 5 illustrates the GPC chart of the phenolic-hydroxyl-group-containing novolac resin (3). The phenolic-hydroxyl-group-containing novolac resin (3) had a number average molecular weight (Mn) of 3,221, a weight average molecular weight (Mw) of 18,778, and polydispersity (Mw/Mn) of 5.83.

Comparative Production Example 1

Production of Phenolic-hydroxyl-Group-Containing Novolac Resin (1')

Figure 6:
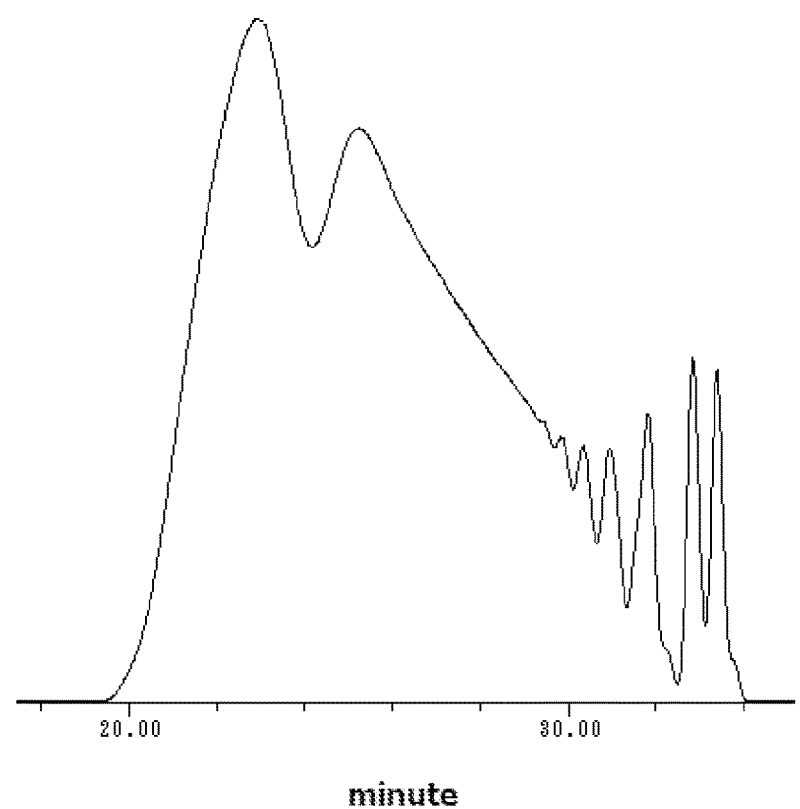
FIG. 6 is a GPC chart of a phenolic-hydroxyl-group-containing novolac resin (1') produced in Comparative Production Example 1.
Figure 7:
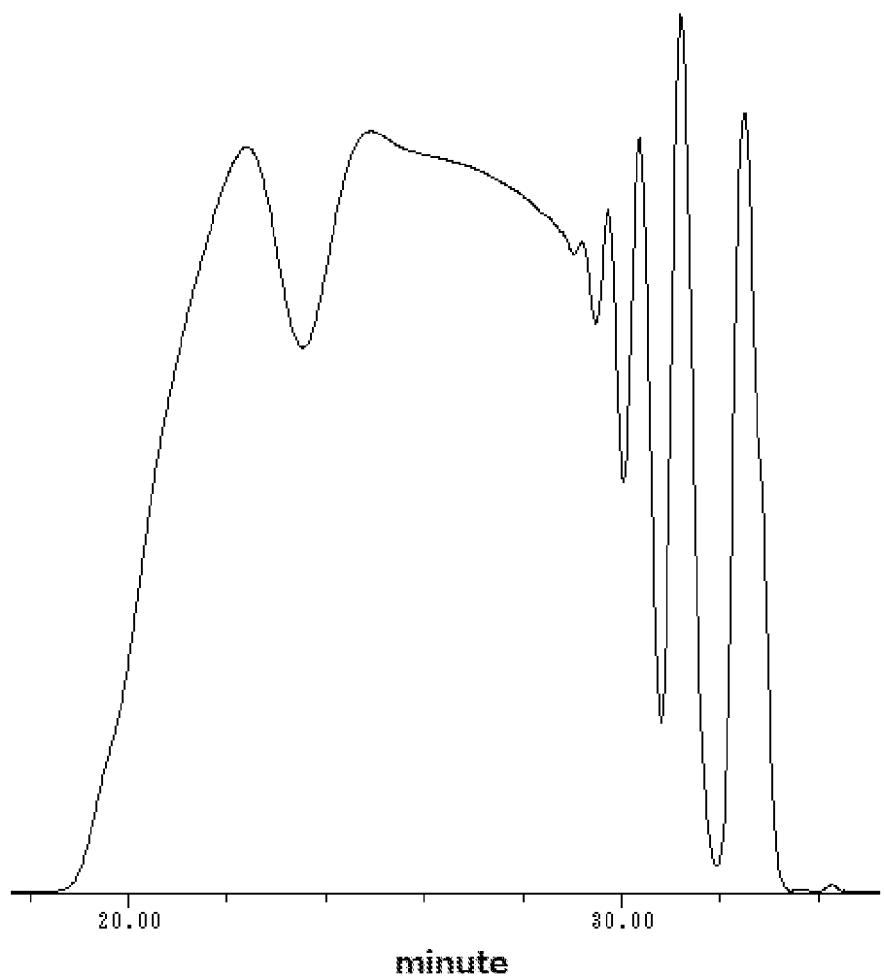
FIG. 7 is a GPC chart of a phenolic-hydroxyl-group-containing novolac resin (2') produced in Comparative Production Example 2.

Into a 300-ml four-neck flask equipped with a cooling pipe, 13.0 g (0.12 mol) of metacresol, 8.6 g (0.08 mol) of paracresol, and 6.1 g (0.02 mol) of 3-pentadecylphenol were put. The content was dissolved in 15 ml of 2-ethoxyethanol and 15 ml of acetic acid. Then, 10 ml of sulfuric acid was added thereto under cooling in an ice bath, and 6.5 g (0.2 mol) of 92% paraformaldehyde was subsequently added thereto. The resulting solution was heated to 80° C. in an oil bath, and the solution was subjected to a reaction under heating and stirring for 10 hours. After the reaction, water was added to the resulting solution to reprecipitate a crude product. The crude product was re-dissolved in acetone and then reprecipitated in water. The precipitate was subsequently separated by filtration and dried under reduced pressure to yield 24.6 g of a phenolic-hydroxyl-group-containing novolac resin (1') of yellow powder. FIG. 6 illustrates the GPC chart of the phenolic-hydroxyl-group-containing novolac resin (1'). The phenolic-hydroxyl-group-containing novolac resin (1') had a number average molecular weight (Mn) of 1,792, a weight average molecular weight (Mw) of 11,701, and polydispersity (Mw/Mn) of 6.53.

Comparative Production Example 2

Production of Phenolic-hydroxyl-Group-Containing Novolac Resin (2')

Into a 2-L four-neck flask equipped with a stirrer and a thermometer, 648 g (6 mol) of m-cresol, 432 g (4 mol) of p-cresol, 2.5 g (0.2 mol) of oxalic acid, and 492 g of 42% formaldehyde were put. The content was heated to 100° C. and subjected to a reaction. The resulting product was heated to 200° C. under normal pressure to remove water and to be distilled and then distilled under reduced pressure at 230° C. for 6 hours to produce 736 g of a phenolic-hydroxyl-group-containing novolac resin (2') of a pale yellow solid. The phenolic-hydroxyl-group-containing novolac resin (2') had a number average molecular weight (Mn) of 1,450, a weight average molecular weight (Mw) of 10,316, and polydispersity of (Mw/Mn) of 7.12.

Examples 4 to 6 and Comparative Examples 1 and 2

The phenolic-hydroxyl-group-containing novolac resins produced in Examples 1 to 3 and Comparative Production Examples 1 and 2 were evaluated as follows. Results of the evaluations are shown in Table 1.

Preparation of Photosensitive Composition

In 60 parts by mass of propylene glycol monomethyl ether acetate, 28 parts by mass of the phenolic-hydroxyl-group-containing novolac resins were individually dissolved. Then, 12 parts by mass of a photosensitizer was added to each of the solutions and dissolved. The resulting solution was filtered through a 0.2-μm membrane filter to obtain a photosensitive composition.

The photosensitizer used was "P-200" manufactured by Toyo Gosei Co., Ltd (condensate of 1 mol of 4,4'-[1-[4-[1-(4-hydroxyphenyl)-1methylethyl]phenyl]ethylidene]bisphenol with 2 mol of 1,2-naphthoquinone-2-diazide-5-sulfonyl chloride).

Preparation of Composition for Heat Resistance Test

In 60 parts by mass of propylene glycol monomethyl ether acetate, 28 parts by mass of the phenolic-hydroxyl-group-containing novolac resins were individually dissolved. Each of the solutions was filtered through a 0.2-μm membrane filter to produce a composition for a heat resistance test.

Evaluation of Alkali Developability [ADR (Å/s)] The photosensitive composition obtained as described above was applied onto a 5-inch silicon wafer to a thickness of approximately 1 μm with a spin coater and dried on a hot plate at 110° C. for 60 seconds. Two wafers were prepared in this manner, and one of them was used as "non-exposed sample". The other one was used as "exposed sample"; the exposed sample was irradiated with 100 mJ/cm² of g, h, and i lines with a ghi-line lamp ("Multilight" manufactured by USHIO INC.) and then heated at 140° C. for 60 seconds.

Both the "non-exposed sample" and the "exposed sample" were immersed in an alkaline developer (2.38% aqueous solution of tetramethylammonium hydroxide) for 60 seconds and then dried on a hot plate at 110° C. for 60 seconds. The thickness of each sample was measured before and after the immersion in the developer. The difference in the thickness of the sample between before and after the immersion was divided by 60, and its value was defined as alkali developability [ADR (Å/s)].

Evaluation of Photosensitivity

The photosensitive composition obtained as described above was applied onto a 5-inch silicon wafer to a thickness of approximately 1 μm with a spin coater and dried on a hot plate at 110° C. for 60 seconds. To this wafer, a mask for a resist pattern of lines and spaces was attached, in which the lines had widths of 1 to 10 μm by 1 μm and the widths of the lines and spaces were 1:1. The resulting wafer was subsequently exposed to g, h, and i lines with a ghi-line lamp ("Multilight" manufactured by USHIO INC.) and heated at 140° C. for 60 seconds. The resulting product was immersed in an alkaline developer (2.38% aqueous solution of tetramethylammonium hydroxide) for 60 seconds and then dried on a hot plate at 110° C. for 60 seconds.

The amount of the exposure to g, h, and i lines was increased from 30 mJ/cm² by 5 mJ/cm², and the amount of the exposure (Eop amount of exposure) that enabled accurate formation of a line having a width of 3 μm was evaluated.

Evaluation of Resolution

The photosensitive composition obtained as described above was applied onto a 5-inch silicon wafer to a thickness of approximately 1 μm with a spin coater and dried on a hot plate at 110° C. for 60 seconds. A photomask was placed on the resulting wafer, and then 200 mJ/cm² of g, h, and i lines were radiated thereto as in Evaluation of Alkali Developability for alkaline development. The state of the formed pattern was observed with a laser microscope ("VK-X200" manufactured by KEYENCE CORPORATION). A pattern resolved at L/S of 5 μm was evaluated as A, and a pattern not resolved at L/S of 5 μm was evaluated as B.

Evaluation of Heat Resistance

The composition for a heat resistance test, which had been produced as described above, was applied onto a 5-inch silicon wafer to a thickness of approximately 1 μm with a spin coater and dried on a hot plate at 110° C. for 60 seconds. The resin content was collected from the wafer, and the glass transition temperature (Tg) of the resin was measured. The glass transition temperature (Tg) was measured with a differential scanning calorimeter (DSC) "Q100" manufactured by TA Instruments) under a nitrogen atmosphere at a temperature ranging from −100 to 250° C. and a temperature increase of 10° C. per minute.

Conformability to Substrates

The photosensitive composition obtained as described above was applied onto a 5-inch silicon wafer to a thickness of approximately 50 μm with a spin coater and dried on a hot plate at 110° C. for 300 seconds. The surface of the wafer was observed with a laser microscope ("VK-X200" manufactured by KEYENCE CORPORATION). A wafer without cracks was evaluated as A, and a wafer with cracks was evaluated as B.

Flexibility

The photosensitive composition obtained as described above was applied onto a 50-μm-thick polyimide film to a thickness of approximately 5 μm with a spin coater and dried on a hot plate at 110° C. for 300 seconds. The laminated film produced was bent to 180 degrees, and the bend was observed with a laser microscope ("VK-X200" manufactured by KEYENCE CORPORATION). A film without cracks was evaluated as A, and a film with cracks was evaluated as B.

TABLE 1

|  |  | Example 4 | Example 5 | Example 6 | Comparative Example 1 | Comparative Example 2 |
|---|---|---|---|---|---|---|
| Phenolic-hydroxyl-group-containing resin | | (1) | (2) | (3) | (1') | (2') |
| Alkali developability | "Non-exposed sample" | 0 | 0 | 0 | 0 | 0 |
| | "Exposed sample" | 2100 | 1000 | 1800 | 80 | 240 |
| Photosensitivity [mJ/cm²] | | 100 | 100 | 100 | >600 | 450 |
| Resolution | | A | A | A | B | B |
| Heat Resistance [° C.] | | 211 | 193 | 198 | 83 | 128 |
| Conformability to Substrates | | A | A | A | A | A |
| Flexibility | | A | A | A | A | A |

Examples 7 to 9 and Comparative Examples 3 and 4

The phenolic-hydroxyl-group-containing novolac resins produced in Examples 1 to 3 and Comparative Production Examples 1 and 2 were evaluated as follows. Results of the evaluations are shown in Table 2.

Preparation of Curable Composition

In 30 parts by mass of propylene glycol monomethyl ether acetate, 16 parts by mass of the individual phenolic-hydroxyl-group-containing novolac resins and 4 parts by mass of a curing agent (1,3,4,6-tetrakis(methoxymethyl) glycoluril manufactured by Tokyo Chemical Industry Co., Ltd.) were dissolved. The solution was filtered through a 0.2-μm membrane filter to obtain a curable composition.

Preparation of Composition for Heat Resistance Test

In 60 parts by mass of propylene glycol monomethyl ether acetate, 28 parts by mass of the phenolic-hydroxyl-group-containing novolac resins were individually dissolved. Each of the solutions was filtered through a 0.2-μm membrane filter to produce a composition for a heat resistance test.

Evaluation of Alkali Developability [ADR (Å/s)]

The curable composition obtained as described above was applied onto a 5-inch silicon wafer to a thickness of approximately 1 μm with a spin coater and dried on a hot plate at 110° C. for 60 seconds. Two wafers were prepared in this manner, and one of them was used as "non-cured sample". The other one was used as "cured sample"; the cured sample was heated at 160° C. for 60 seconds.

Both the "non-cured sample" and the "cured sample" were immersed in an alkaline developer (2.38% aqueous solution of tetramethylammonium hydroxide) for 60 seconds and then dried on a hot plate at 110° C. for 60 seconds. The thickness of each sample was measured before and after the immersion in the developer. The difference in the thickness of the sample between before and after the immersion was divided by 60, and its value was defined as alkali developability [ADR (Å/s)].

Evaluation of Heat Resistance

The curable composition produced as described above was applied onto a 5-inch silicon wafer to a thickness of approximately 1 μm with a spin coater and dried on a hot plate at 110° C. for 60 seconds and then heated at 160° C. for 60 seconds. The resin content was collected from the wafer, and the glass transition temperature (Tg) of the resin was measured. The glass transition temperature (Tg) was measured with a differential scanning calorimeter (DSC) "Q100" manufactured by TA Instruments) under a nitrogen atmosphere at a temperature ranging from −100 to 250° C. and a temperature increase of 10° C. per minute.

Conformability to Substrates

The curable composition obtained as described above was applied onto a 5-inch silicon wafer to a thickness of approximately 50 μm with a spin coater and dried on a hot plate at 110° C. for 300 seconds. The surface of the wafer was observed with a laser microscope ("VK-X200" manufactured by KEYENCE CORPORATION). A wafer without cracks was evaluated as A, and a wafer with cracks was evaluated as B.

The invention claimed is:

1. A phenolic-hydroxyl-group-containing novolac resin that is a polycondensate of which essential reactive components are a phenolic-hydroxyl-group-containing compound (A) represented by Structural Formula (1)

[Chem. 1]

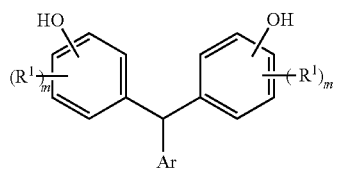

(1)

[where Ar is a structural part represented by Structural Formula (Ar-1) or (Ar-2)

[Chem. 2]

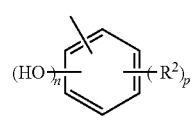

(Ar-1)

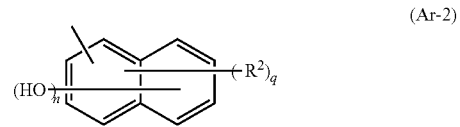

(Ar-2)

(where n in each formula is independently an integer from 0 to 2; p is an integer from 0 to 5; q is an integer from 0 to 7; and $R^2$ in each formula is independently a hydrogen atom, an alkyl group, an alkoxy group, an aryl group, an aralkyl group, or a halogen atom);

$R^1$'s are each independently a hydrogen atom, an alkyl group, an alkoxy group, an aryl group, an aralkyl group, or a halogen atom; and m's are each independently an integer from 0 to 4], a phenolic-hydroxyl-group-containing compound (B) represented by Structural Formula (2)

TABLE 2

|  | | Example 7 | Example 8 | Example 9 | Comparative Example 3 | Comparative Example 4 |
|---|---|---|---|---|---|---|
| Phenolic-hydroxyl-group-containing resin | | (1) | (2) | (3) | (1') | (2') |
| Alkali developability | "Non-cured sample" | 1900 | 870 | 1600 | 50 | 200 |
|  | "Cured sample" | 0 | 0 | 0 | 0 | 0 |
| Heat Resistance [° C.] | | >250 | >250 | >250 | 119 | 156 |
| Conformability to Substrates | | A | A | A | A | A |

[Chem. 3]

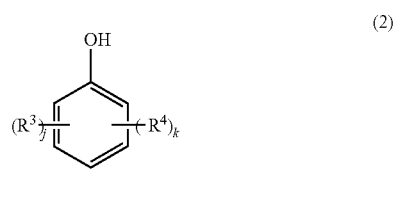

[where R³ is an aliphatic hydrocarbon group having 8 to 16 carbon atoms; j is an integer from 1 to 3; R⁴ is each independently a hydrogen atom, an alkyl group having 1 to 3 carbon atoms, an alkoxy group, an aryl group, an aralkyl group, or a halogen atom; k is an integer from 0 to (5-j)], and an aldehyde compound (C).

2. The phenolic-hydroxyl-group-containing novolac resin according to claim 1, wherein the molar ratio of the phenolic-hydroxyl-group-containing compound (A) to the phenolic-hydroxyl-group-containing compound (B) [(A):(B)] is in the range of 100:0.1 to 100:30.

3. The phenolic-hydroxyl-group-containing novolac resin according to claim 1, wherein the resin has a polydispersity (Mw/Mn) ranging from 3 to 10.

4. The phenolic-hydroxyl-group-containing novolac resin according to claim 1, wherein the resin has a weight average molecular weight (Mw) ranging from 10,000 to 30,000.

5. A curable composition comprising the phenolic-hydroxyl-group-containing novolac resin and a curing agent; wherein the phenolic-hydroxyl-group-containing novolac resin is a polycondensate of which essential reactive components are a phenolic-hydroxyl-group-containing compound (A) represented by Structural Formula (1)

[Chem. 1]

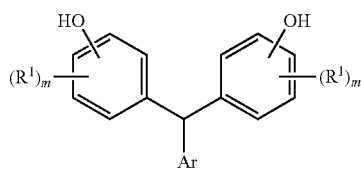

[where Ar is a structural part represented by Structural Formula (Ar-1) or (Ar-2)

[Chem. 2]

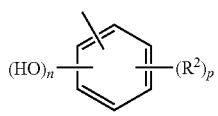

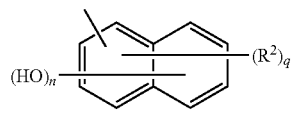

(where n in each formula is independently an integer from 0 to 2; p is an integer from 0 to 5; q is an integer from 0 to 7; and R² in each formula is independently a hydrogen atom, an alkyl group, an alkoxy group, an aryl group, an aralkyl group, or a halogen atom);

R¹'s are each independently a hydrogen atom, an alkyl group, an alkoxy group, an aryl group, an aralkyl group, or a halogen atom; and m's are each independently an integer from 0 to 4], a phenolic-hydroxyl-group-containing compound (B) represented by Structural Formula (2)

[Chem. 3]

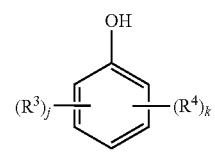

[where R³ is an aliphatic hydrocarbon group having 4 to 20 carbon atoms; j is an integer from 1 to 3; R⁴ is each independently a hydrogen atom, an alkyl group having 1 to 3 carbon atoms, an alkoxy group, an aryl group, an aralkyl group, or a halogen atom; k is an integer from 0 to (5-j)], and an aldehyde compound (C).

6. A cured product that is produced by curing the curable composition according to claim 5.

7. The curable composition according to claim 5, wherein the molar ratio of the phenolic-hydroxyl-group-containing compound (A) to the phenolic-hydroxyl-group-containing compound (B) [(A):(B)] is in the range of 100:0.1 to 100:30.

8. A cured product that is produced by curing the curable composition according to claim 7.

9. The curable composition according to claim 5, wherein the phenolic-hydroxyl-group-containing novolac resin has a weight average molecular weight (Mw) ranging from 10,000 to 30,000.

10. A cured product that is produced by curing the curable composition according to claim 9.

11. The curable composition according to claim 5, wherein the phenolic-hydroxyl-group-containing novolac resin has a polydispersity (Mw/Mn) ranging from 3 to 10.

12. A cured product that is produced by curing the curable composition according to claim 11.

13. The curable composition according to claim 5, wherein R³ in Structural Formula (2) is an aliphatic hydrocarbon group having 8 to 16 carbon atoms.

14. A cured product that is produced by curing the curable composition according to claim 13.

\* \* \* \* \*